US007748384B2

United States Patent
Ho et al.

(10) Patent No.: US 7,748,384 B2
(45) Date of Patent: *Jul. 6, 2010

(54) PATIENT INTERFACE WITH FOREHEAD AND CHIN SUPPORT

(75) Inventors: Peter Chi Fai Ho, Pittsburgh, PA (US); Lance Busch, Trafford, PA (US); Jian An Jiang, Shezhen (CN)

(73) Assignee: RIC Investments, LLC, Wilmington, DE (US)

( * ) Notice: Subject to any disclaimer, the term of this patent is extended or adjusted under 35 U.S.C. 154(b) by 1037 days.

This patent is subject to a terminal disclaimer.

(21) Appl. No.: 11/411,578

(22) Filed: Apr. 26, 2006

(65) Prior Publication Data

US 2006/0191539 A1    Aug. 31, 2006

Related U.S. Application Data

(63) Continuation of application No. 10/953,642, filed on Sep. 29, 2004, now Pat. No. 7,047,971.

(60) Provisional application No. 60/508,574, filed on Oct. 3, 2003.

(51) Int. Cl.
*A61M 16/00* (2006.01)
*B62B 9/00* (2006.01)

(52) U.S. Cl. ............... 128/207.11; 128/207.13; 128/207.17; 128/201.22; 128/205.25; 128/206.21

(58) Field of Classification Search ........ 128/207.11, 128/207.13, 207.17, 207.18, 201.22, 201.23, 128/201.24, 207.27, 204.18, 206.21, 206.24, 128/206.28, 848; 2/171, 171.2, 173

See application file for complete search history.

(56) References Cited

U.S. PATENT DOCUMENTS

| 1,843,585 | A | * | 2/1932 | Orman ............................ 2/9 |
| 2,065,410 | A | * | 12/1936 | Woloson .......................... 2/9 |
| 4,907,584 | A | | 3/1990 | McGinnis |
| 5,243,971 | A | | 9/1993 | Sullivan et al. |
| 5,361,416 | A | | 11/1994 | Petrie et al. |
| 5,517,986 | A | | 5/1996 | Starr et al. |

(Continued)

FOREIGN PATENT DOCUMENTS

WO    WO 00/78384 A1    12/2000

OTHER PUBLICATIONS

Map Medizin-Technologie GmbH, Instruction Manual for Papillon®, 2002.

(Continued)

*Primary Examiner*—Justine R Yu
*Assistant Examiner*—Clinton Ostrup
(74) *Attorney, Agent, or Firm*—Michael W. Haas

(57) ABSTRACT

A patient interface gas delivery mask having a forehead and chin support system including a forehead support, a chin support, and a system for supplying a flow of gas to a patient that incorporates such a mask, forehead support, and chin support. The forehead support includes a supporting arm which is adjustably mounted to the mask shell, thereby allowing the adjustment of the distance between the forehead support bracket and the mask shell in order to adjust for patient's of different sizes. A forehead support bracket is pivotally connected to the support arm. Likewise the chin support is also adjustably mounted to the mask shell.

20 Claims, 18 Drawing Sheets

U.S. PATENT DOCUMENTS

| | | | |
|---|---|---|---|
| 5,560,354 A * | 10/1996 | Berthon-Jones et al. | 128/205.25 |
| 5,570,689 A | 11/1996 | Starr et al. | |
| 6,119,693 A | 9/2000 | Kwok et al. | |
| 6,119,694 A * | 9/2000 | Correa et al. | 128/207.13 |
| 6,357,441 B1 | 3/2002 | Kwok et al. | |
| 6,412,488 B1 | 7/2002 | Barnett et al. | |
| 6,463,931 B1 | 10/2002 | Kwok et al. | |
| 6,467,483 B1 | 10/2002 | Kopacko et al. | |
| 6,651,663 B2 | 11/2003 | Barnett et al. | |
| 6,860,269 B2 | 3/2005 | Kwok et al. | |
| 2004/0025883 A1 | 2/2004 | Eaton et al. | |
| 2004/0045551 A1 | 3/2004 | Eaton et al. | |
| 2004/0083534 A1 * | 5/2004 | Ruiz et al. | 2/171.2 |
| 2005/0011522 A1 | 1/2005 | Ho et al. | |
| 2005/0039753 A1 | 2/2005 | Schumacher | |

OTHER PUBLICATIONS

Map Medizin-Technologie GmbH, Instruction Manual for Papillon®.

* cited by examiner

PATIENT INTERFACE WITH FOREHEAD AND CHIN SUPPORT

CROSS-REFERENCE TO RELATED APPLICATIONS

This application is a Continuation of and claims priority under 35 U.S.C. §120 from U.S. patent application Ser. No. 10/953,642, which claims priority under 35 U.S.C. §119(e) from provisional U.S. patent application No. 60/508,574 filed Oct. 3, 2003 the contents of each which are incorporated herein by reference.

BACKGROUND OF THE INVENTION

1. Field of the Invention

The present invention generally relates to a patient interface device for use in a pressure support system that supplies a flow of gas to the airway of a patient, and, in particular to a patient interface device that includes a forehead and a chin support system and to a pressure support system that includes such a patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that in order for the mask to maintain a seal without any undue gas leaks around the periphery of the mask, the mask may be compressed against the patient's face. This is most notable, for example, in masks having a bubble type cushion. While the bubble cushion itself is comfortable, it does not provide adequate support which may cause gas leaks around the periphery of the mask. The bubble effect is diminished when the headgear strap force is increased to improve stability.

It is known to provide a patient interface device that includes a forehead support that contacts the patient's forehead to provide a support mechanism between the mask and the patient's forehead. Gas delivery masks having forehead cushions, spacers or supports are described, for example, in U.S. Pat. Nos. 4,907,584; 5,243,971; 5,517,986; 5,570,689; 6,119,693; and 6,357,441; 6,467,483. The forehead supports prevent the mask from exerting too much force on a patient's face and provides stability to the mask.

Another mask with forehead support is disclosed in International Publication No. WO 00/78384 A1. In this arrangement a forehead support is adapted to be secured to a respiratory mask. The forehead support includes a joining member for securing to the mask and a cushion frame pivotally mounted to the joining member.

However, an advantage exists for increased stability of the gas delivery mask support. Another advantage exists for a support which evenly distributes headgear strapping force by utilizing both forehead and chin supports. A further advantage exists for increased isolation of the gas delivery mask support from the mask cushion.

SUMMARY OF THE INVENTION

An exemplary embodiment of the present invention comprises a patient interface device having a forehead support assembly and a chin support assembly, both of which are coupled to a mask shell. In a further embodiment, including adjustably controlling a position of the forehead support assembly, the chin support assembly, or both relative to the mask shell.

An exemplary embodiment of the present invention, the forehead support assembly includes a forehead support arm operatively coupled to the mask shell and a forehead support bracket mounted on the forehead support arm, and the chin support assembly includes a chin support arm operatively coupled to the mask shell and a chin support bracket mounted on the chin support arm. This configuration for the patient interface device provides adjustment along an axis or curve which is normal to the plane of the mask shell to adjust for patients of different sizes and shapes. The adjustment assembly allows a patient to adjust the mask in such a way as to minimize leakage and pressure on certain areas of the face, such as the nose bridge.

Like forehead supports, the chin support of the present invention provides relief of pressure and improved stability. Additionally, the chin support of the present invention eliminates the unpleasant pressure on the cheek area common with known strapping arrangements. Also, the relocation of the mounting force below the cushion (unlike current arrangements with the mounting force situated along the center line of the cushion) helps to stabilize the mask. When wearing a nasal mask, the chin support helps eliminate leak in the area above the lips. In oral-nasal masks, seal capability is improved.

These features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
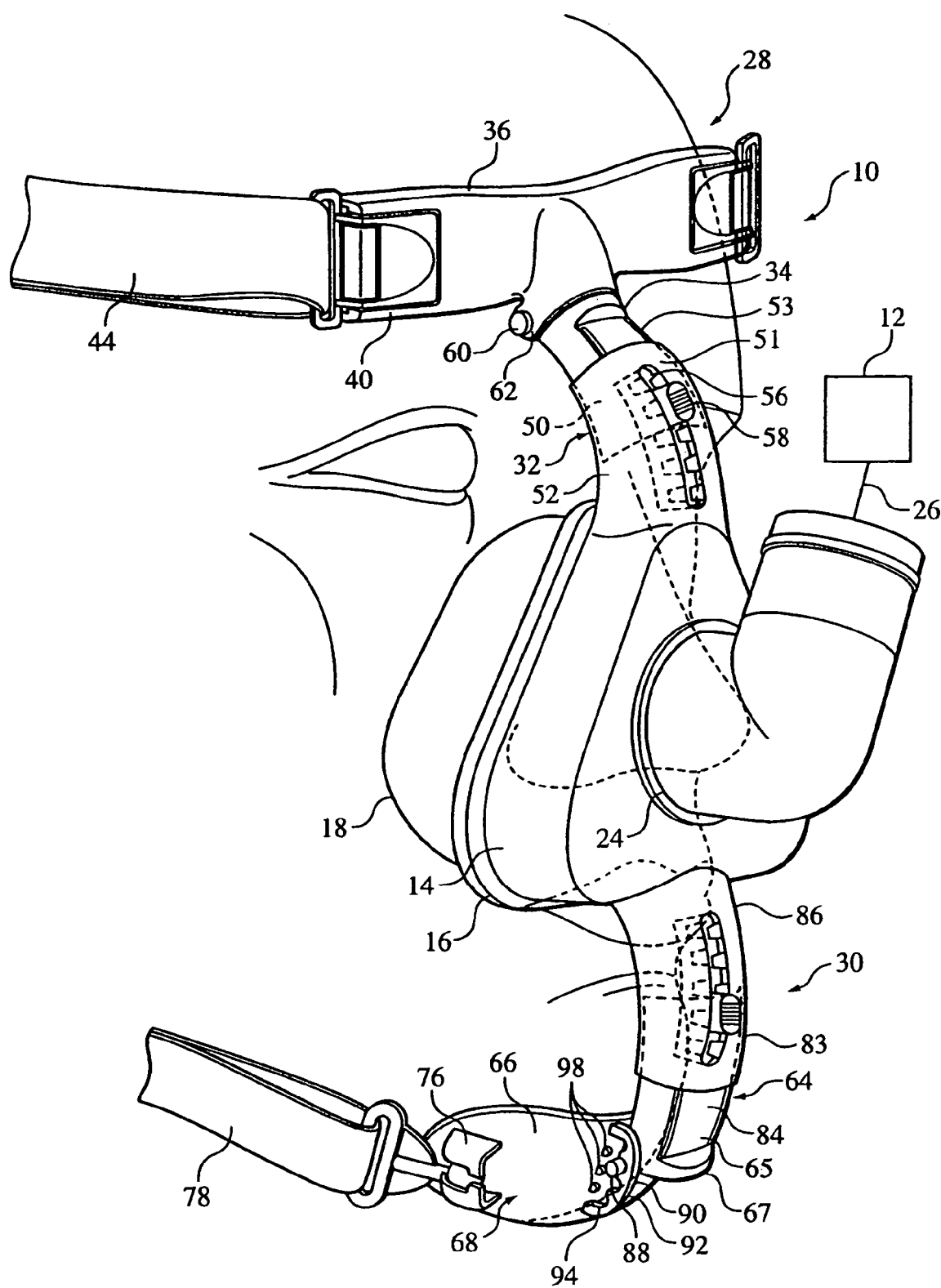
FIG. 1 is a perspective view of the patient interface device according to the principles of the present invention shown (schematically) connected to a gas flow generating system.
Figure 2:
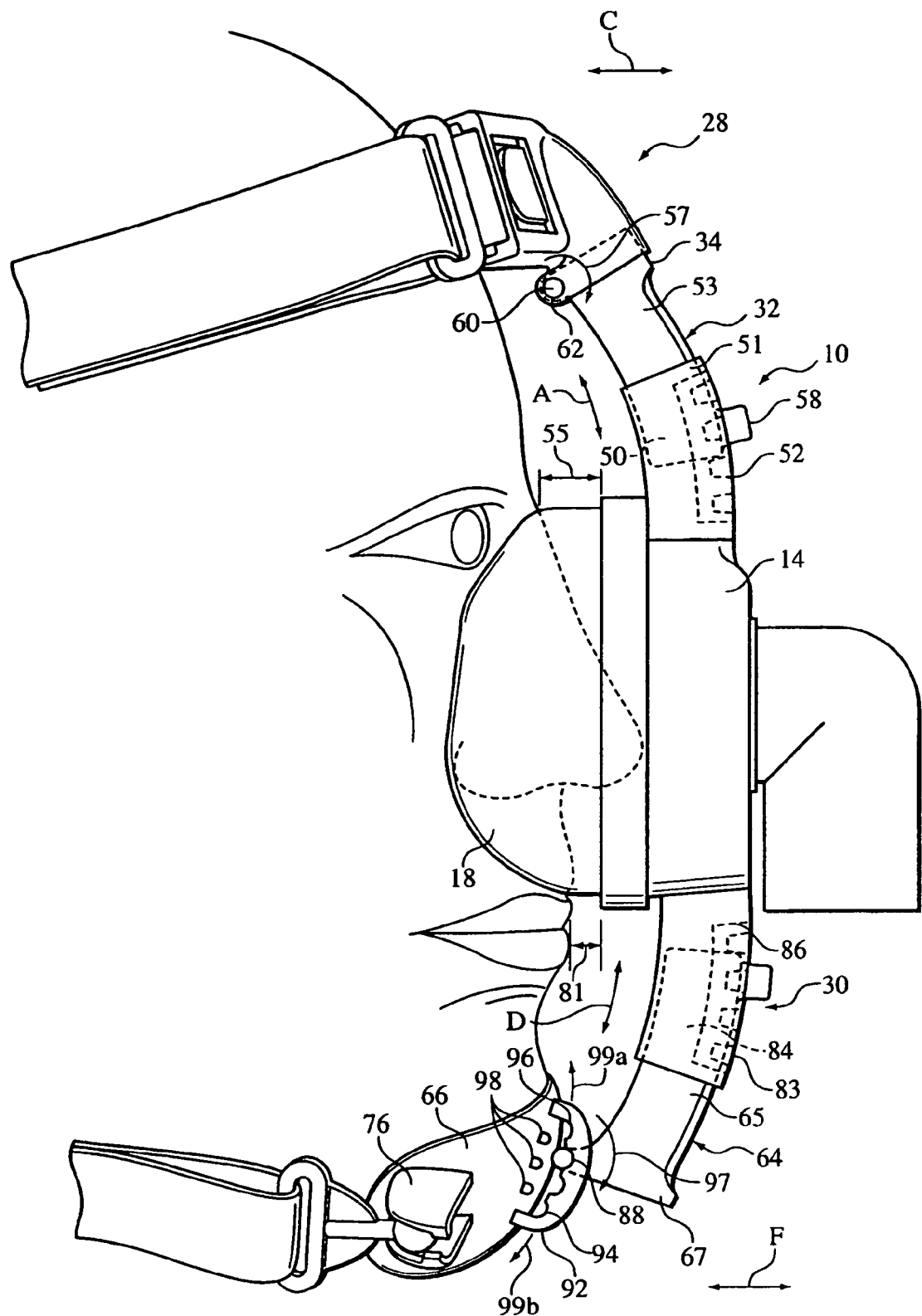
FIG. 2 is a side view of the patient interface device of FIG. 1.

In describing the presently preferred embodiments of the invention, the terms "horizontal" and "vertical" refer to the orientation of the mask as illustrated in the accompanying drawings. More specifically, "horizontal" refers to a left-right or side-to-side direction, and "vertical" refers to an up-down or top-bottom direction.

FIGS. 1-4 illustrate an exemplary embodiment of a patient interface device according to the principles of the present invention. These figures illustrate a patient interface device 10 that communicates a flow of breathing gas between a patient's airway and a pressure generating device 12, such as a ventilator, CPAP device, or variable pressure device, e.g. an auto-titrating device, proportional assist ventilation (PAV) device, proportional positive airway pressure (PPAP) device, C-Flex device, Bi-Flex device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device. It should be noted that the term "mask" or "mask assembly" is also used herein to refer to the patient interface device.

Referring to FIGS. 1-4, patient interface device 10 includes a mask shell 14 or body portion, which is preferably, but not necessarily, a generally rigid, formed structural shell having an open side that defines an annular portion 16 to which a resilient, relatively soft cushion or seal member 18 is attached. In the illustrated exemplary embodiment, mask shell 14 is substantially triangular in shape, having an upper apex 20 and two lower angles 22. Mask shell 14 includes an inlet opening 24 adapted to receive a gas supply conduit 26, which is also referred to in the art as a patient circuit. It is to be understood that the present invention contemplates that the mask shell can have any shape suitable to serve as a patient interface. Mask shell 14 is preferably formed from rigid plastic, such as polycarbonate. Seal member 18 is configured to contact a portion of the patient, such as the area of the face surrounding the nose, so that a portion of the patient, such as the nose, is received within the cavity defined within the mask shell. Alternatively, patient interface 10 may, instead, comprise a nasal/oral mask configured to enclose the nose and mouth of a patient or an oral mask configured to enclose only the mouth of a patient.

Mask shell 14 is essentially supported on the patient's face by a forehead support assembly, generally indicated at 28, and a chin support assembly, generally indicated at 30. Forehead support assembly 28, which, according to the illustrated exemplary embodiment, is generally T-shaped, includes a forehead support arm 32 and a forehead support bracket 36 attached thereto. In the illustrated exemplary embodiment, the forehead support bracket is coupled to an upper end portion 34 of forehead support arm 33. Forehead support arm 32 can be attached to forehead support bracket 36 in a fixed fashion or in an adjustable fashion. The latter configuration is illustrated in FIGS. 1-4, and is discussed in greater detail below.

A pair of forehead pads 38 are provided on the patient contacting side of forehead support bracket 36. Forehead pads 38 form the actual contact point of forehead assembly 28 to the patient's forehead. As such, the forehead pads are preferably made from a material that is biocompatible and comfortable to the touch. In an exemplary embodiment of the present invention, the forehead pads are formed from an elastomeric cushioning material, such as silicon.

In the illustrated embodiment, the forehead pads 38 comprise two pads, one mounted on each of the end portions 40 of the forehead support bracket 36. Also, the forehead pads have a generally semi-cylindrical shape. The present invention contemplates the forehead pads 38 can be any suitable cushioning element and may include a single pad and/or different sizes or variations or formed from alternative materials such as gel, foam, or silicone. Examples of other forehead pads suitable for use in the present invention are described in U.S. patent application Ser. No. 10/884,060 (publication no. US-2005-0011522-A1), the contents of which are incorporated herein by reference.

Each end portion 40 of the forehead support bracket, preferably includes a connector element 42 (FIG. 3) for securing an upper headgear strap 44. In this preferred embodiment, connector element 42 is a female receiving slot for receiving a male quick release element 46 attached to an upper headgear strap 44. However, it should be understood that other connection mechanisms can be used to attach the headgear to the forehead support bracket, including the ball and socket configuration for securing a lower headgear strap to the chin support assembly. The ball and socket configuration, and other headgear attachment configurations suitable for use with the present invention, are disclosed in co-pending U.S.

patent application Ser. No. 10/629,366, the contents of which are incorporated herein by reference.

Figure 3:
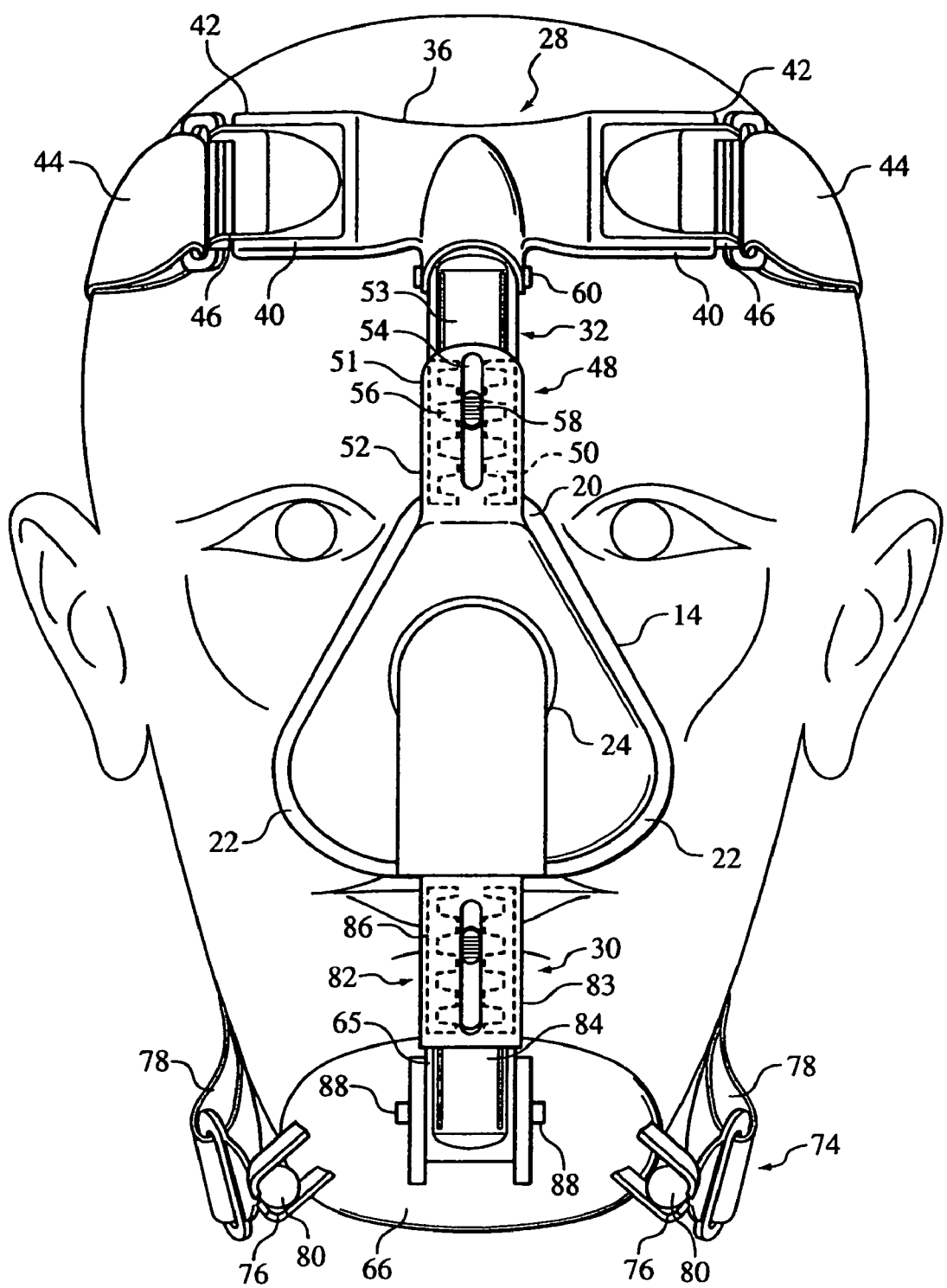
FIG. 3 is a front view of the patient interface device of FIG. 1.
Figure 4:
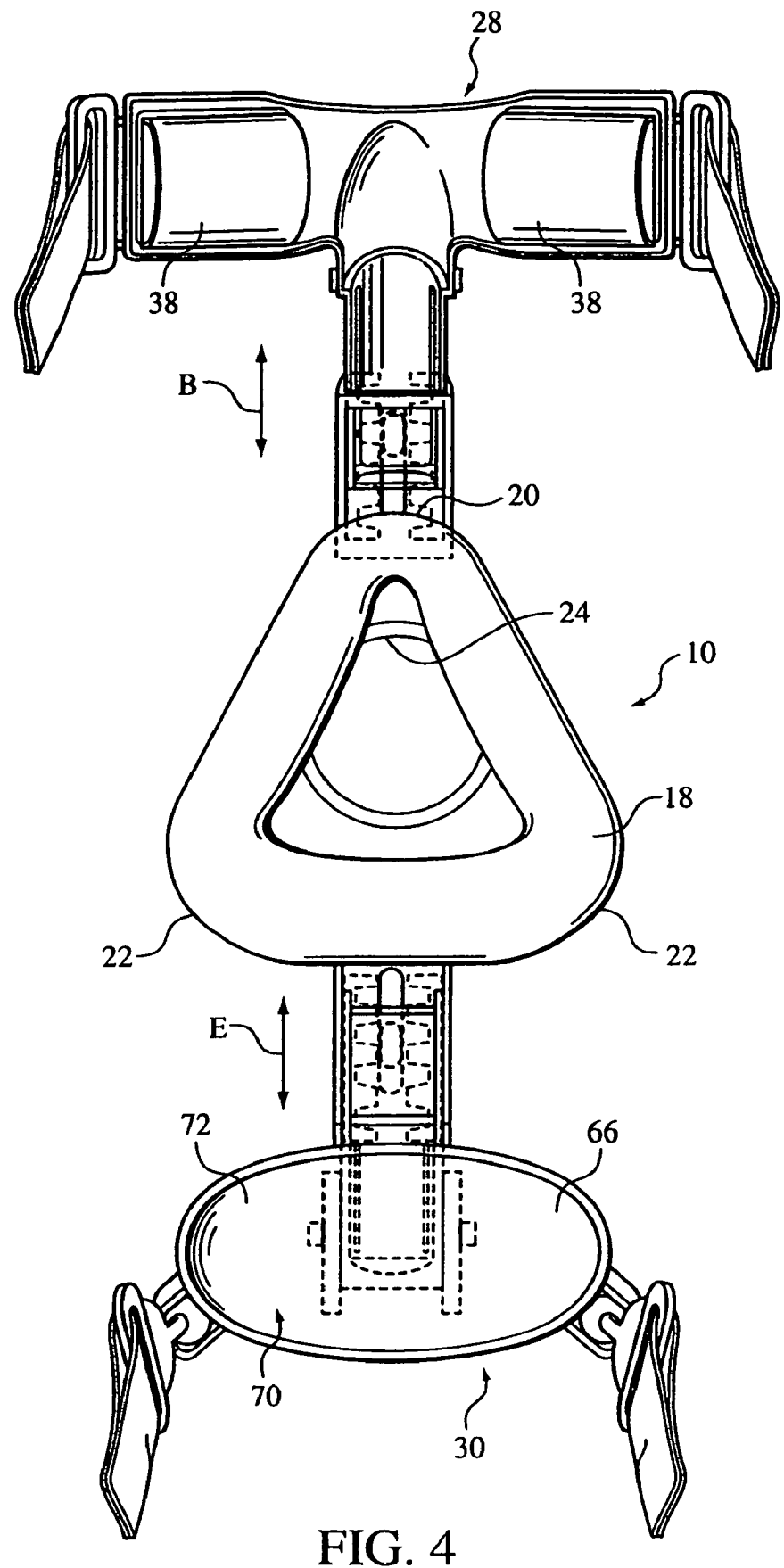
FIG. 4 is a back view of the patient interface device of FIG. 1.

Forehead support assembly 28 further includes a forehead adjustment assembly, generally indicated at 48 in FIG. 3, to provide adjustment of forehead support bracket 36 relative to mask shell 14. In the embodiment illustrated in FIGS. 1-4, forehead adjustment assembly provides adjustment of the forehead support assembly along an axis or curve, as indicated by arrow A in FIG. 2, to allow the patient interface to be adjusted to accommodate patients of different sizes, shapes, and comfort desires. Forehead adjustment assembly 48 allows a patient to adjust the mask in such a way as to minimize leakage and pressure on certain areas of the face, such as the nose bridge, as discussed below. The present invention contemplates that any one of a wide variety of adjustment mechanisms can be used to adjust forehead support bracket 36 relative to mask shell 14. Several of these mechanisms are illustrated in the present application.

In the embodiment illustrated in FIGS. 1-4, forehead adjustment assembly 48 is defined by components that also define forehead support arm 32. That is, forehead support arm 32 includes an arcuate attaching member 52 and an arcuate support member 53. An end portion 50 of arcuate support member 53 is slidably coupled to an upper end portion 51 of arcuate attaching member 52, so that forehead support bracket 36 is adjustably connectable to mask shell 14. Arcuate attaching member 52 is coupled to mask shell 14 and extends from a central portion of the mask shell above inlet opening 24 to a position spaced above upper apex angle 20 of the mask shell. Arcuate attaching member 52 has a generally tubular cross section having an exterior guide slot 54 having opposed ratchet-like teeth 56.

Arcuate support member 53 of support arm 32 also has a generally tubular cross section, is adapted to slide within arcuate attaching member 52, and has a central protrusion 58 corresponding to guide slot 54. Central protrusion 58 is located on a flexible member having ratchet teeth (not illustrated) on either side either of the central protrusion. When central protrusion 58 is depressed, the flexible member flexes allowing the ratchet teeth to disengage from each other so that arcuate support member 53 and attaching member 52 can move relative to each other.

The present invention contemplates a different number of opposed teeth could be used, as well as the teeth could be on the bracket portion and the protrusion could be on the shell portion. In the illustrated embodiment, arcuate support member 53 is integral with mask shell 14. It is to be further understood, however, that an adjustable coupling can be provided between these two components. Also, these components need not be integrally joined.

It can be appreciated from the above description and the accompanying illustrations, that forehead adjustment assembly 48 of the present invention allows forehead support assembly 28, including forehead support arm 32, forehead support bracket 36, and forehead pads 38, to move relative to mask shell 14 in two general directions simultaneously. First, the entire forehead support assembly 28 moves in a generally vertical direction, i.e., in a direction parallel to the plane in which the mask shell 14 lies, to move forehead pads 38 closer to or away from mask shell 14, as indicated by arrow B in FIG. 4. Second, the entire forehead support 28 moves in a generally horizontal direction, i.e., in a direction generally perpendicular to the plane in which mask shell 14 lies, as indicated by arrow C, in FIG. 2.

This simultaneous, two dimensional movement is made possible by the curvilinear shape of forehead adjustment assembly 48, and, more particularly, the curvilinear shape of attaching member 52 and support member 53. This allows forehead support assembly 28 to be adjusted for the optimal, i.e., most comfortable, fit on the patient. More specifically, movement of the forehead support relative to the mask shell in this manner has the effect of controlling a distance 55 (See FIG. 2) between the patient and mask shell 14 at upper apex 20. Controlling distance 55, in turn, primarily controls the force that the cushion exerts on the surface of the patient at the bridge of the nose. Because the bridge of the nose is a particularly sensitive area for many patients, allowing adjustment of the mask shell at upper apex 20 via forehead support assembly 28, allows the patient to have a great degree of control over the mask comfort and fit.

As noted above, the present invention contemplates providing an adjustable connection between forehead support arm 32 and forehead support bracket 36. This is accomplished in the present embodiment by providing a pivoting coupling between these two elements. More specifically, protruding pivot mounts 60 are provided on opposite sides of arcuate support member 53. Forehead support bracket 36 includes a pair of corresponding openings 62, so that pivot mounts 60 are pivotally receivable within the openings 62. This configuration allows forehead support bracket 36 to pivot relative to forehead support arm 32 about an axis through pivot mounts 60, as indicated by arrow 57 in FIG. 2.

In the illustrated embodiment, this pivoting movement is not lockable, so that the forehead support bracket will naturally seek its ideal position relative to the forehead support arm when the forehead support assembly is positioned on the patient. It is to be understood, however, that the present invention contemplates providing a locking mechanism so that the position of the forehead support bracket relative to the forehead support arm can be locked. In addition, the pivoting structure shown in the figures and described above is subject to variations. For example, the pivot mounts can be provided on the forehead support bracket and the opening for the mounts provided on the forehead support arm.

Chin support assembly 30, according to the illustrated exemplary embodiment, is generally T-shaped and includes a chin support arm 64 and a chin support bracket 66. In the illustrated embodiment, chin support bracket 66 is a substantially rigid cup-shaped member that includes an outer surface 68 opposite an inner surface 70. Inner surface 70 is preferably concave-shaped to receive the chin of the patient. A soft padding piece 72 is preferably attached to the inner surface for increased comfort and stability.

In the illustrated exemplary embodiment, chin support assembly 30 includes a lower headgear connector assembly 74, which includes a pair of first connectors 76 rigidly attached to chin support bracket 66. Lower headgear straps 78 of the headgear assembly are selectively connected to patient interface device 10 by means of second connectors 80. In the illustrated embodiment, a pair of second connectors 80, are removably connectable to end portions of headgear straps 78 and are also removably connectable to first connectors 76 on each side of the chin support bracket 66. In the illustrated embodiment, first and second connectors 76 and 80 are ball-and-socket connectors corresponding to those disclosed in U.S. patent application Ser. No. 10/629,366 (publication no. US-2004-0025883-A1). It is to be understood, however, that the present invention contemplates using any conventional connection assembly for attaching the lower headgear to the chin support assembly.

Like forehead support assembly 28, chin support assembly 30 also includes a chin adjustment assembly, generally indicated at 82 in FIG. 3. More specifically, chin adjustment assembly 82 provides adjustment of the chin adjustment assembly along an axis or curve, as indicated by arrow D in FIG. 2, to allow the patient interface to be adjusted to accommodate patients of different sizes, shapes, and comfort desires. Chin adjustment assembly 82 allows a patient to adjust the mask in such a way as to minimize leakage and pressure on certain areas of the face, such as the nose bridge, as discussed below. The present invention contemplates that any one of a wide variety of adjustment mechanisms can be used to adjust chin support bracket 36 relative to mask shell 14. Several of these mechanisms are illustrated in the present application.

Chin adjustment assembly 82 illustrated in this embodiment, allows chin support bracket 66 to move relative to mask shell 14 in two general directions simultaneously. First, chin support bracket 66 moves in a generally vertical direction, i.e., in a direction parallel to the plane in which the mask shell 14 lies, to move chin support bracket 66 closer to or away from mask shell 14, as indicated by arrow E in FIG. 4. Second, chin support bracket 66 moves in a generally horizontal direction, i.e., in a direction generally perpendicular to the plane in which mask shell 14 lies, as indicated by arrow F, in FIG. 2.

In the embodiment illustrated in FIGS. 1-4, chin adjustment assembly 82 is defined by components that also define chin support arm 64. That is, chin support arm 64 includes an arcuate attaching member 86 and an arcuate support member 65. An end portion 84 of arcuate support member 65 is slidably coupled to an end portion 83 of arcuate attaching member 86, so that chin support bracket 66 is adjustably connectable to mask shell 14. Arcuate attaching member 86 is coupled to mask shell 14 and extends from a central portion of the mask shell below inlet opening 24.

Arcuate attaching member 86 and arcuate support member 65 of chin support arm 64 are connected to each other using a ratchet-type connection like that used in forehead support arm 32. Thus, the details of the ratchet-type connection between mask shell 14 and chin support bracket 66 are omitted for the sake of brevity. In addition, arcuate attaching member 86 and arcuate support member 65 have complimentary tubular shapes to provide a stable, yet adjustable, coupling between these two member.

This simultaneous, two dimensional movement is made possible by the curvilinear shape of chin adjustment assembly 82, and, more particularly, the curvilinear shape of attaching member 86 and support member 65. This allows chin support assembly 30 to be adjusted for the optimal, i.e., most comfortable, fit on the patient. More specifically, movement of the chin support relative to the mask shell in this manner has the effect of controlling a distance 81 (See FIG. 2) between the patient and mask shell 14 at a lower portion thereof. Controlling distance 81, in turn, primarily controls the force that the cushion exerts on the surface of the patient below the nose.

In the illustrated exemplary embodiment, chin support bracket 66 is adjustably connected to an end portion 67 of arcuate support member 65 in chin support arm 54 via a slide-and-rotate arrangement. That is, chin support bracket 66 can both slide and rotate with respect to chin support arm 64. To achieve this dual functionality, end portion 67 of the chin support arm includes protruding pivot axis 88 on opposite sides thereof. Outer surface 68 of chin support bracket 66 includes a pair of corresponding arcuate members 90 having an outer edge 92 and an inner edge 94. Inner edge 94 includes at least one and, in this illustrated embodiment, four grooves 96 in which pivot axis 88 is receivable. Outer surface 68 of chin support bracket 66 further includes protrusions 98 opposite grooves 96, and which lay along a preset locus. Pivot axis 88 slides along inner edge 94 between grooves 96, so that the chin support bracket 66 can move independently of the motion of chin support arm 64 with respect to mask shell 14.

It can be appreciated that this configuration for the chin support bracket provides three independent positional adjustments for the chin support bracket relative to the mask shell. First, the chin support bracket moves in a lengthwise direction along attaching member 86, as indicated by arrow D. Second, the chin support bracket moves in a sliding direction within inner edge 94 between the grooves, as indicated by arrows 99a and 99b in FIG. 2. Finally, the chin support bracket pivots about axis 88, as indicated by arrow 97.

The present invention contemplates the headgear that can be used with the patient interface device can be any suitable headgear, i.e., any conventional headgear used in the patient interface field. For example, a typical headgear assembly comprises a headpiece (not shown) that overlies a portion of the patient's crania and with a pair of lower headgear straps and a pair of upper headgear straps extending therefrom to adjustably connect the headgear to the mask.

Alternative exemplary embodiments of the patient interface device of the present invention are illustrated in FIGS. 5-18. In these embodiments, many features are similar to those illustrated in FIGS. 1-4. Thus, the description of these embodiments will focus primarily on the features of the patient interface device unique to each embodiment. These alternative embodiments are provided primarily to show the different configurations that are possible for the mask shell and cushion, the forehead and chin support assemblies, and sub-components thereof. It is to be understood that the present application contemplates mixing and matching the features of the patient interface device illustrated in all of these embodiments. For example, the chin support assembly of FIG. 7 can be used in conjunction with the forehead support assembly of FIG. 1.

Figure 5:
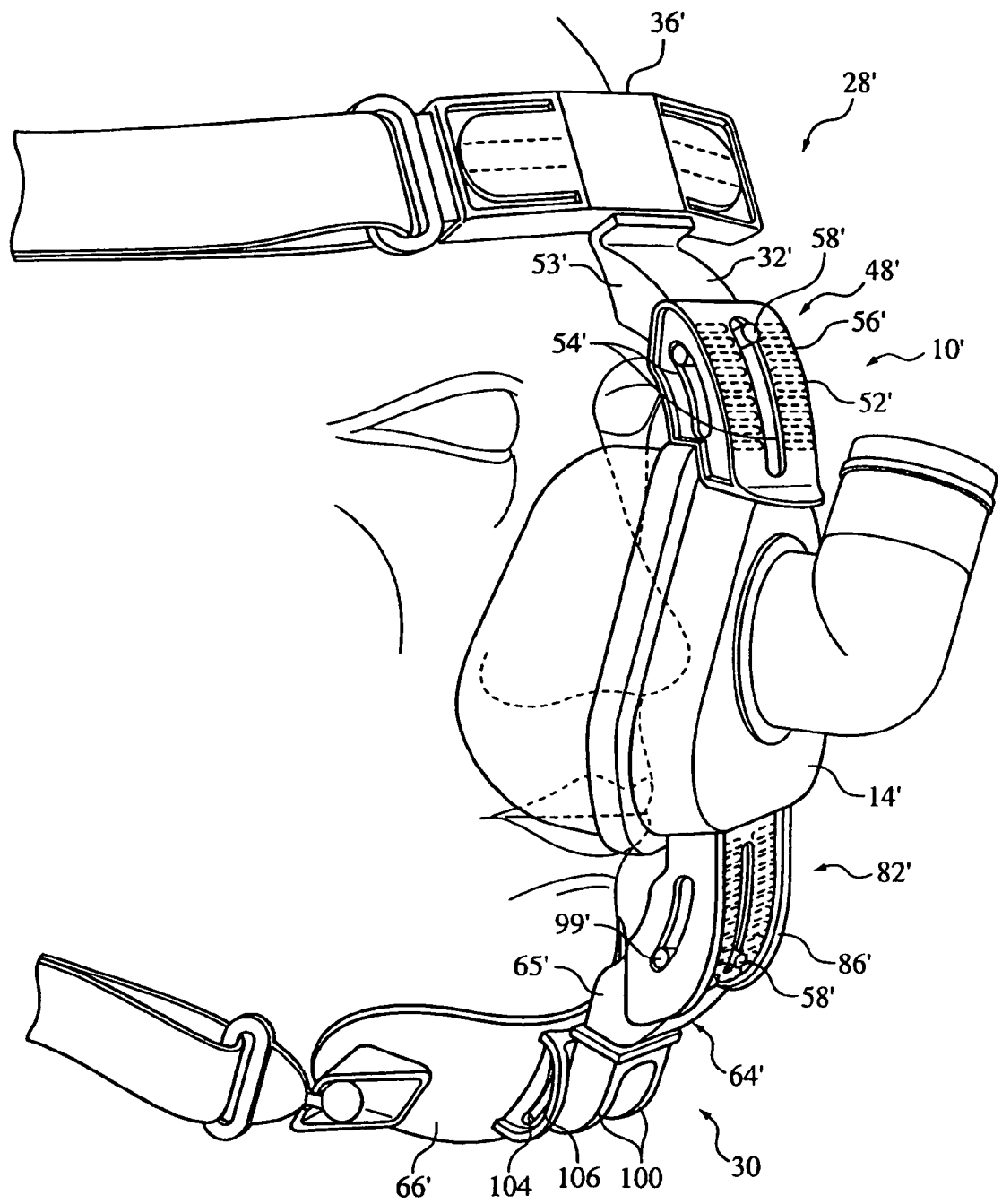
FIG. 5 is a perspective view of a second embodiment of a patient interface device according to the present invention.
Figure 6:
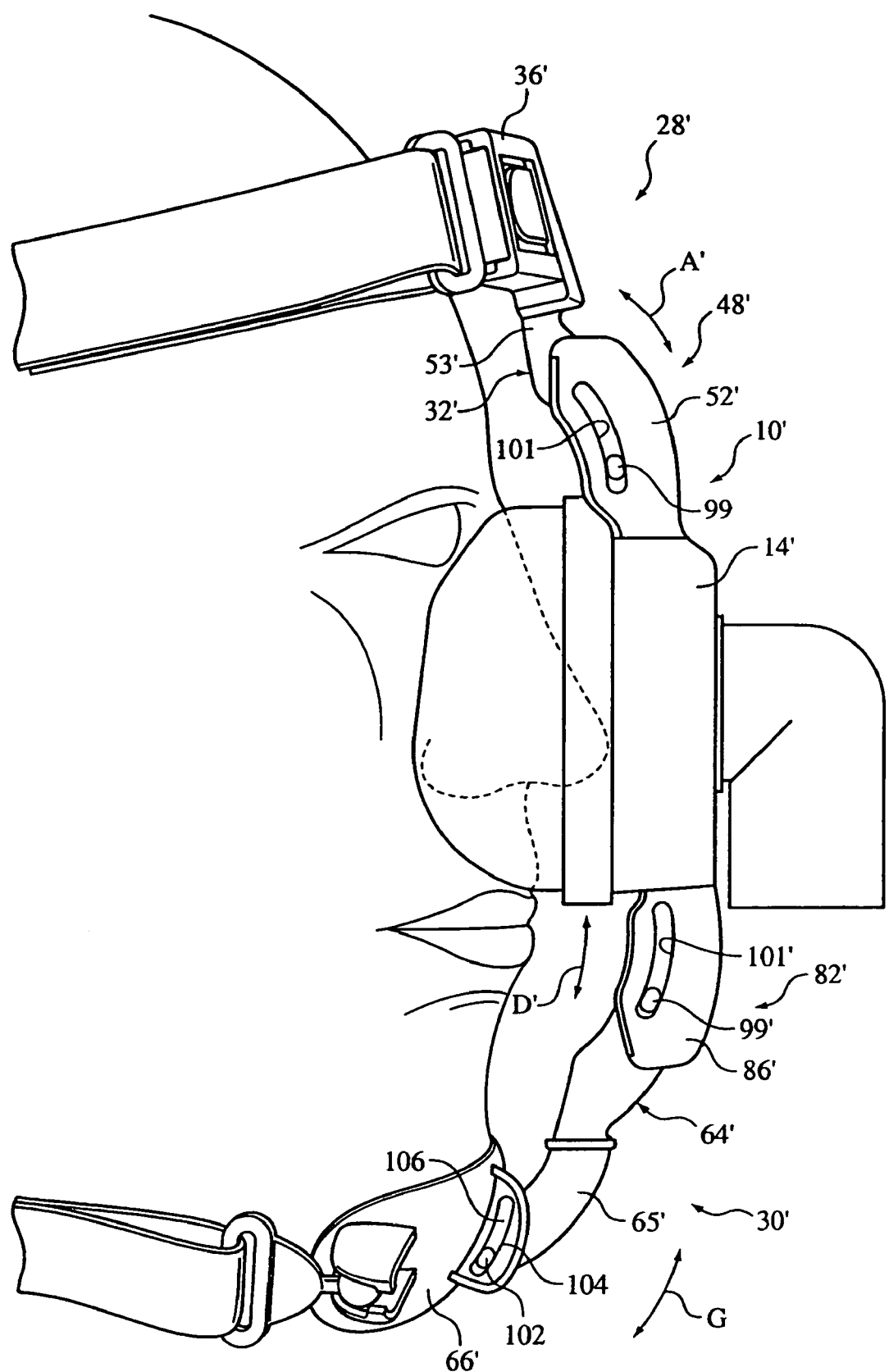
FIG. 6 is a side view of the patient interface device of FIG. 5.

Like in the embodiment of FIGS. 1-4, patient interface device 10' of the second embodiment illustrated in FIGS. 5 and 6 includes a forehead support assembly 28' having forehead adjustment assembly 48' to provide adjustment of forehead support bracket 36' relative to mask shell 14. In this embodiment, forehead adjustment assembly 48' includes arcuate attaching member 52' and arcuate support member 53', both of which define forehead support arm 32' and both of which have generally U-shaped cross sections that are connected to each other using a ratchet-type connection. Attaching member 52' has guide slots 54' on each side of its U-shape. Central guide slot 54' has opposed ratchet-like teeth 56'. Support member 53' is adapted to slide within arcuate attaching member 52' and has a central protrusion 58' corresponding to the central guide slot 54' along with guide protrusions 99 corresponding to the other two guide slots 101 (only one of which is shown).

Like the embodiment of FIG. 1-4, central protrusion 58' is located on a flexible member corresponding having ratchet teeth (not illustrated) on either side of central protrusion 58'. When central protrusion 58' is pressed inwardly, the flexible member flexes inwardly allowing the ratchet teeth to disengage from each other so that arcuate support member 53' and arcuate attaching member 52' can move relative to each other. In this embodiment, forehead bracket 36' is rigidly coupled to arcuate support member 53'.

Like the chin adjustment assembly of FIGS. 1-4, chin adjustment assembly 82' of FIGS. 5 and 6 includes a chin support assembly 30' that includes a chin support arm 64'. Chin support arm 64' includes an arcuate attaching member 86' and an arcuate support member 65' connected to each other using a ratchet-type connection like that used in the forehead support arm. As with the embodiments of FIGS. 1-4, the relative male-female relationships between the bracket portion and the shell portion of the adjustment assemblies can be reversed.

Unlike the previous embodiment, a lower end portion of chin support arm 64' is generally bifurcated forming two parallel vertical walls 100 each having protrusions 102 on the lower end. An outer surface 68' of chin support bracket 66' includes a pair of corresponding arcuate members 104 forming a pair of arched grooves 106 for receiving the protrusions. Movement of protrusions 102 in grooves 106 causes chin support bracket 66' to move relative to chin support arm 64' in a sliding manner, as indicated by arrow G in FIG. 6. In this manner, the position of chin support bracket 66' relative to chin support arm 64' and mask 14' is allowed to "float" so that the best position for the chin support bracket is achieved without user intervention. This self-aligning feature allows the chin support bracket, for example, to remain parallel to the patient's chin at all times, thus enhancing comfort and stability. It should be emphasized that this "floating" or "self-aligning" functionality can also be used for the forehead support assembly.

Figure 7:
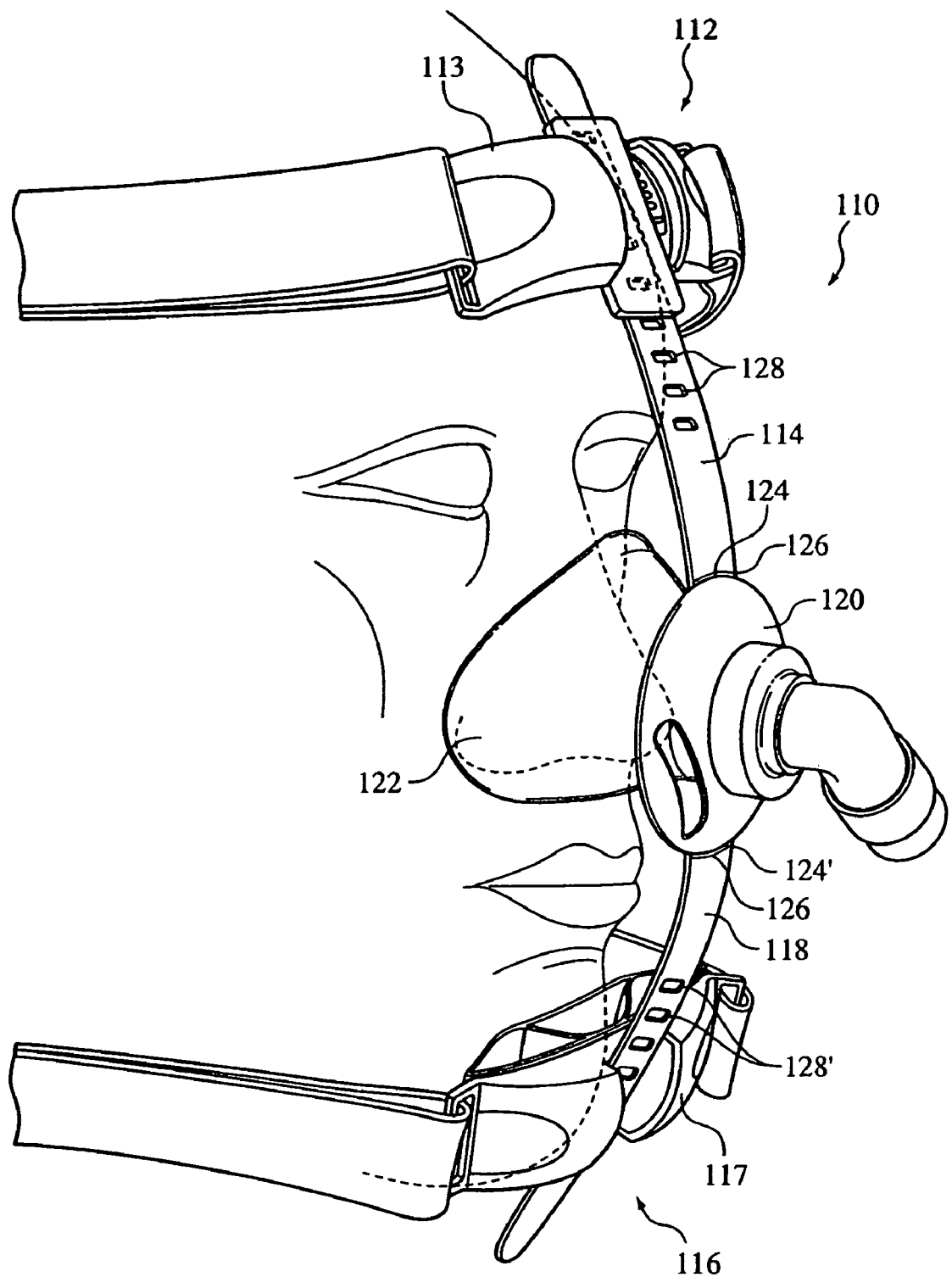
FIG. 7 is a perspective view of a third embodiment of a patient interface device according to the present invention.
Figure 8:
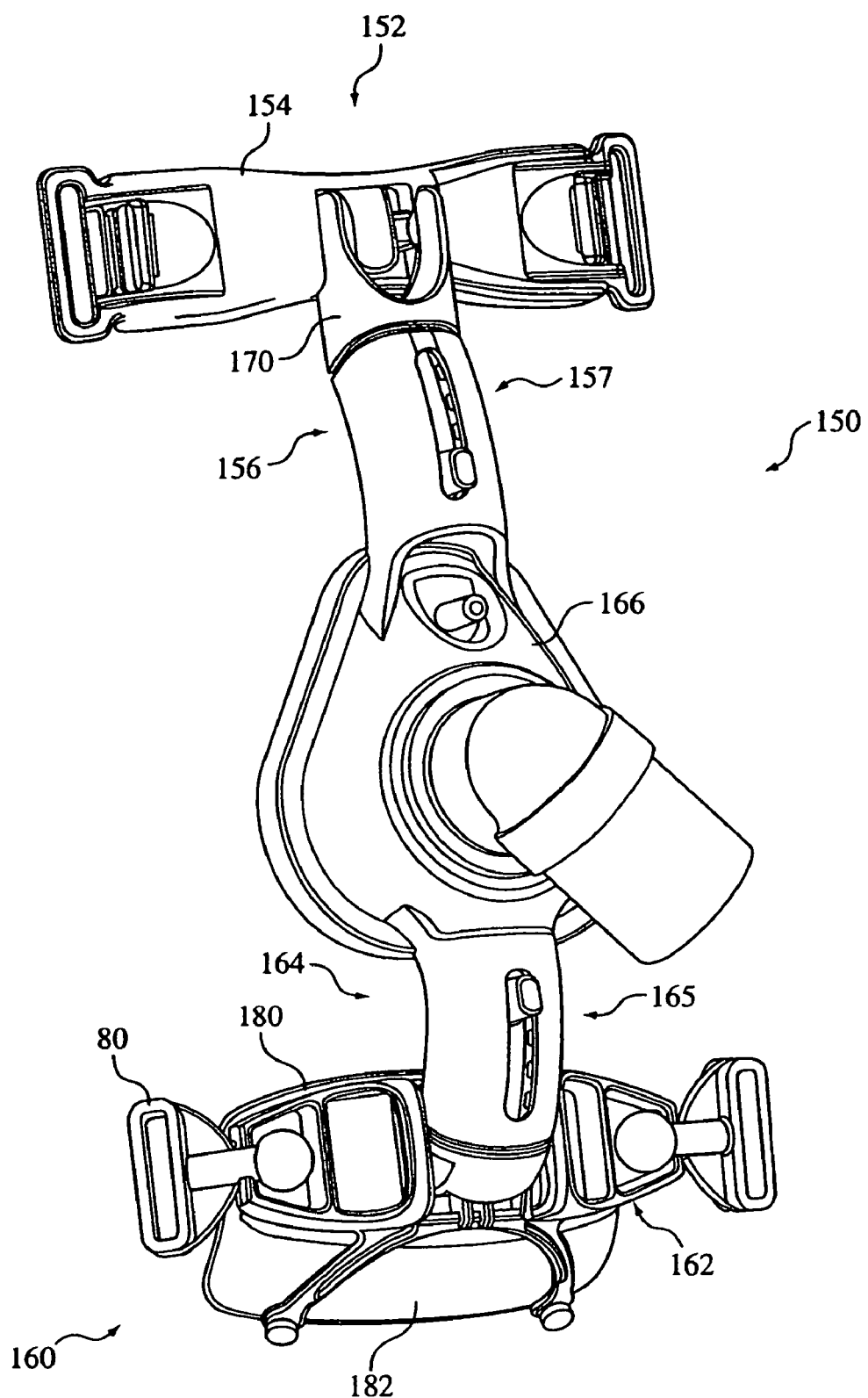
FIG. 8 is a perspective view of a fourth embodiment of a patient interface device according to the present invention.

A third exemplary embodiment for a patient interface device 110 is illustrated in FIG. 7. Like in the previous embodiments, the forehead support assembly in this embodiment includes a forehead adjustment assembly 112 having a forehead support bracket 113 and a forehead support arm 114, and the chin support assembly includes a chin adjustment assembly 116 having chin support bracket 117 and a chin support arm 118. In this illustrated embodiment, the mask shell includes a collar 120. A seal member or cushion 122 is fixed to collar 120 so that the seal member does not move relative to the collar. The present invention also contemplates coupling the seal to the collar in a movable fashion.

Unlike the previous embodiments, forehead support arm 114 and chin support arm 118 single-piece flexible elements attached to opposite sides of collar 120. In the illustrated embodiment, forehead support arm 114 and chin support arm 118 are attached to collar 120 with a living hinge 124, 124' disposed at the attachment point of each support arm with the collar. This configuration allows the forehead and chin support arms to flex and bend to allow for greater flexibility in the attachment of the patient interface device to the user.

In an exemplary embodiment, living hinge 124, 124' includes a notched portion 126, 126' of reduced thickness at the bases of forehead and chin support arms 114 and 118. Each notched portion preferably has a diameter that is oriented generally perpendicular to forehead and chin support arms 114 and 118. Living hinges 110 allow forehead and chin support arms 114 and 118 to flex in a direction perpendicular to the plane in which the collar 120 is oriented.

Forehead and chin support arms 114 and 118 further include adjustment slots 128, 128', which allow forehead and chin support brackets 113 and 117 to slide up and down relative to the forehead and chin support arms for further adjustment. That is, a selectively actuated latching mechanism (not shown), such as an engagement pin disposed on a spring, is provided on forehead and chin support brackets 113 and 117. This latching mechanism engages one or more of the slots on the support arms for locking the support brackets in a fixed position on the support arm. It is to be understood, that other techniques for controlling the position of the support brackets on the support arm, such as a friction lock, are contemplated by the present invention.

In the illustrated exemplary embodiment, collar 120 and seal 122 correspond to the mask assembly described in U.S. Pat. No. 6,412,488, the contents of which are incorporated herein by reference and in U.S. Pat. No. 6,651,663, the contents of which are also incorporated herein by reference. It is to be understood, however, that the present invention contemplates providing other sizes and configurations for collar 120 and seal 122 is shown as a generally circular structure.

In the illustrated embodiment, forehead adjustment assembly 112 and chin adjustment assembly 116 are substantially identical. It is to be understood, however, that the present invention does not require this to be the case. Forehead adjustment assembly 112 and chin adjustment assembly 116 can have different configurations, adjustment portions, pads, etc. For example, the present invention contemplates providing a chin cup, as described in the previous embodiments, as chin support bracket 117.

A fourth exemplary embodiment for a patient interface device 150 is illustrated in FIGS. 8-12. Like in the previous embodiments, this embodiment includes a forehead support assembly 152 having a forehead support bracket 154 and a forehead support arm 156, and a chin support assembly 160 having chin support bracket 162 and a chin support arm 164. In this illustrated embodiment, the forehead and chin support assemblies are connected to a mask shell 166 that includes a chamber for receiving a portion of user's face, such as the nose, and an opening to which the patient circuit 26 is attached. A patient contacting cushion (not shown) is attached to an end portion 168 of mask shell 166 in a fixed or removable fashion.

Forehead support arm 156 includes a forehead adjustment assembly 157 that allows for adjustment of the relative position between forehead support bracket 154 and mask shell 166. Similarly, chin support arm 164 includes a chin adjustment assembly 165 that allows for adjustment of the relative position between chin support bracket 162 and mask shell 166. It is to be understood, however, that either or both the forehead adjustment assembly and chin adjustment assembly can be eliminated from this embodiment (or any other embodiment) in favor of providing a fixed position between the forehead support bracket and mask shell or the chin support bracket and mask shell.

This fourth embodiment for the patient interface device is similar to the first embodiment, except for the attachment of the forehead support bracket to the forehead support arm and the configuration for chin support bracket 162. Thus, the description of this embodiment will focus on these features of patient interface device 150. Again, it is to be understood that the unique features of one embodiment for the patient interface device can be combined with the unique features of other embodiments.

Figure 9:
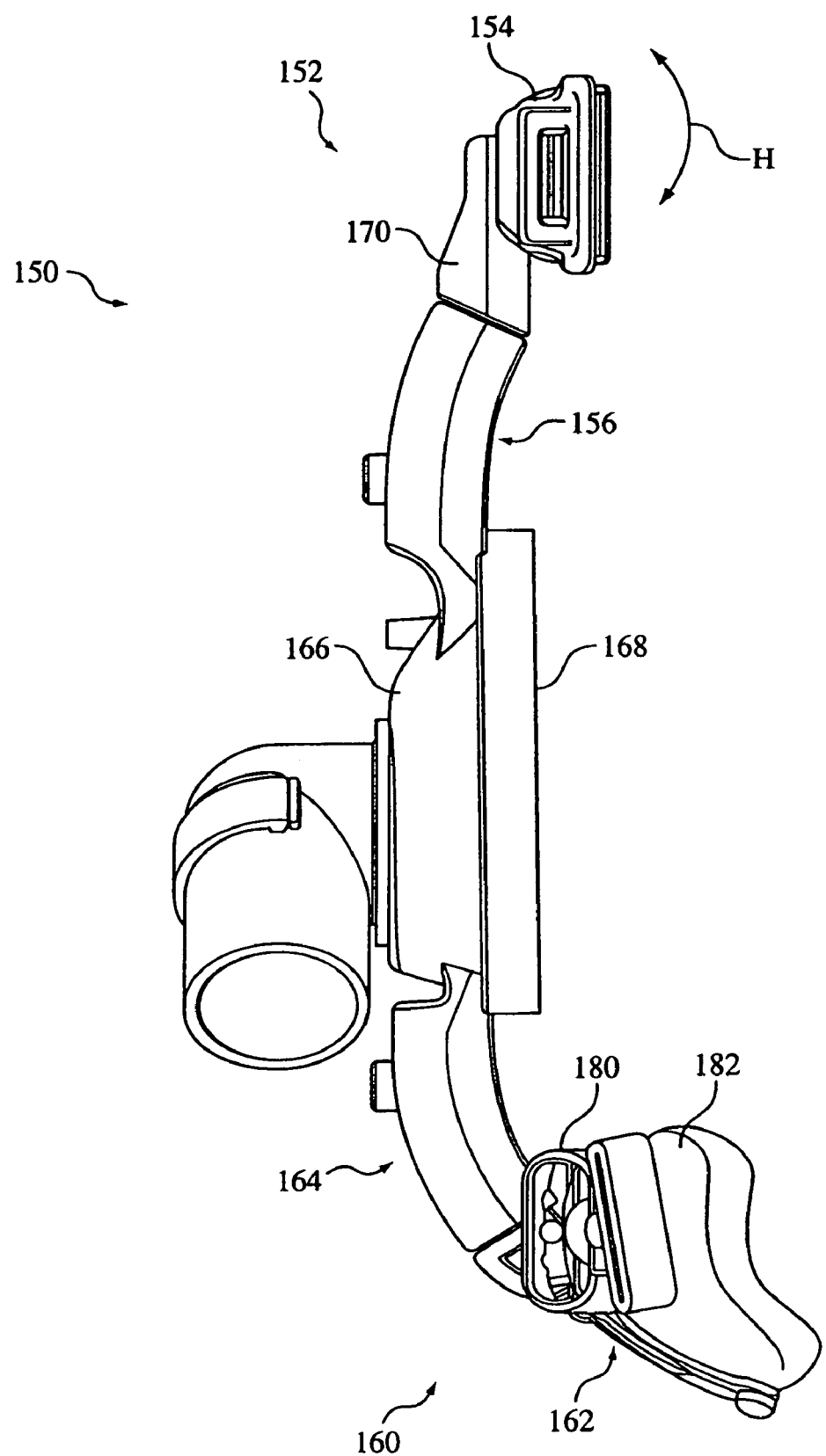
FIG. 9 is a side of the patient interface device of FIG. 8.
Figure 10:
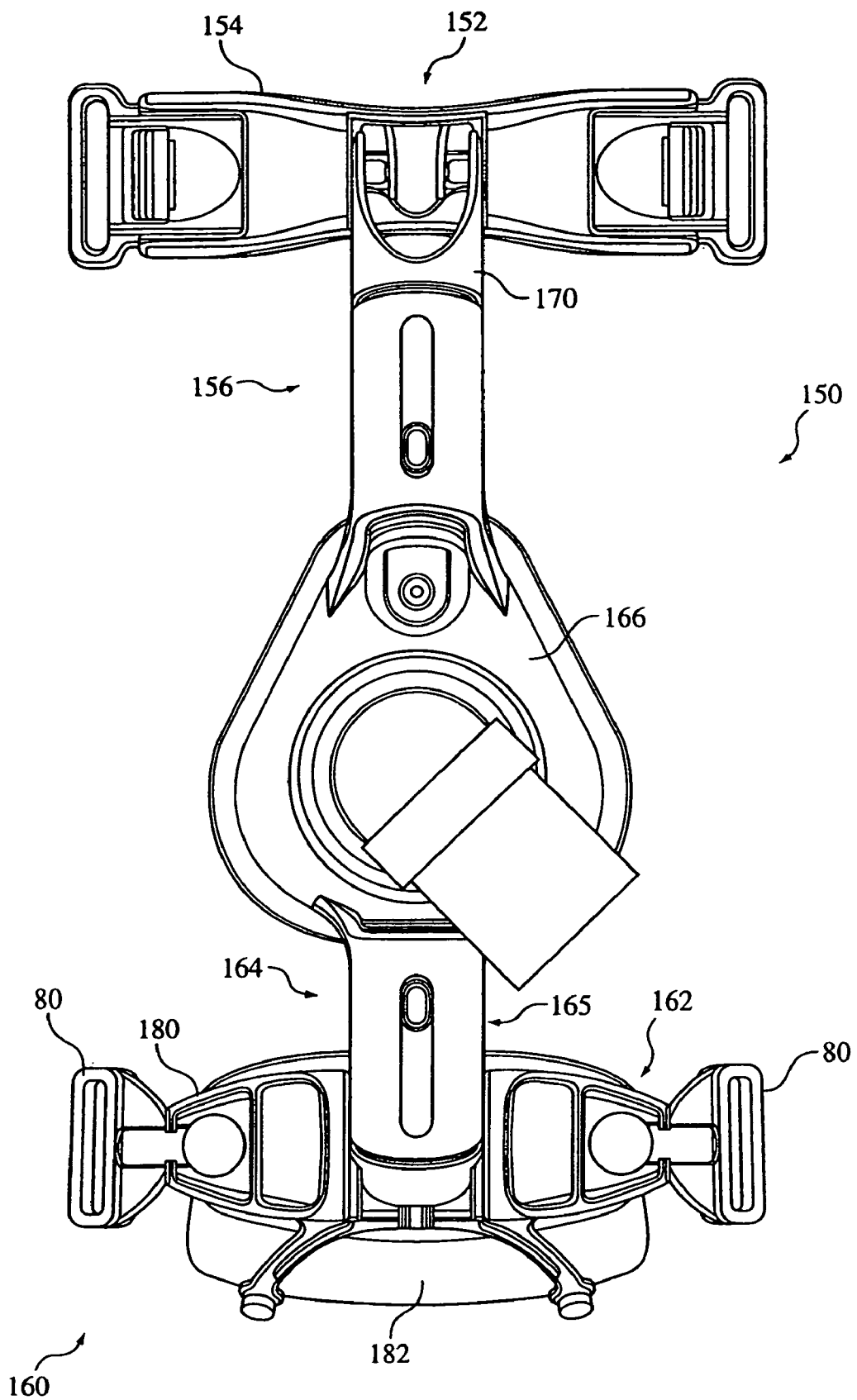
FIG. 10 is a front view of the patient interface device of FIG. 8.
Figure 11:
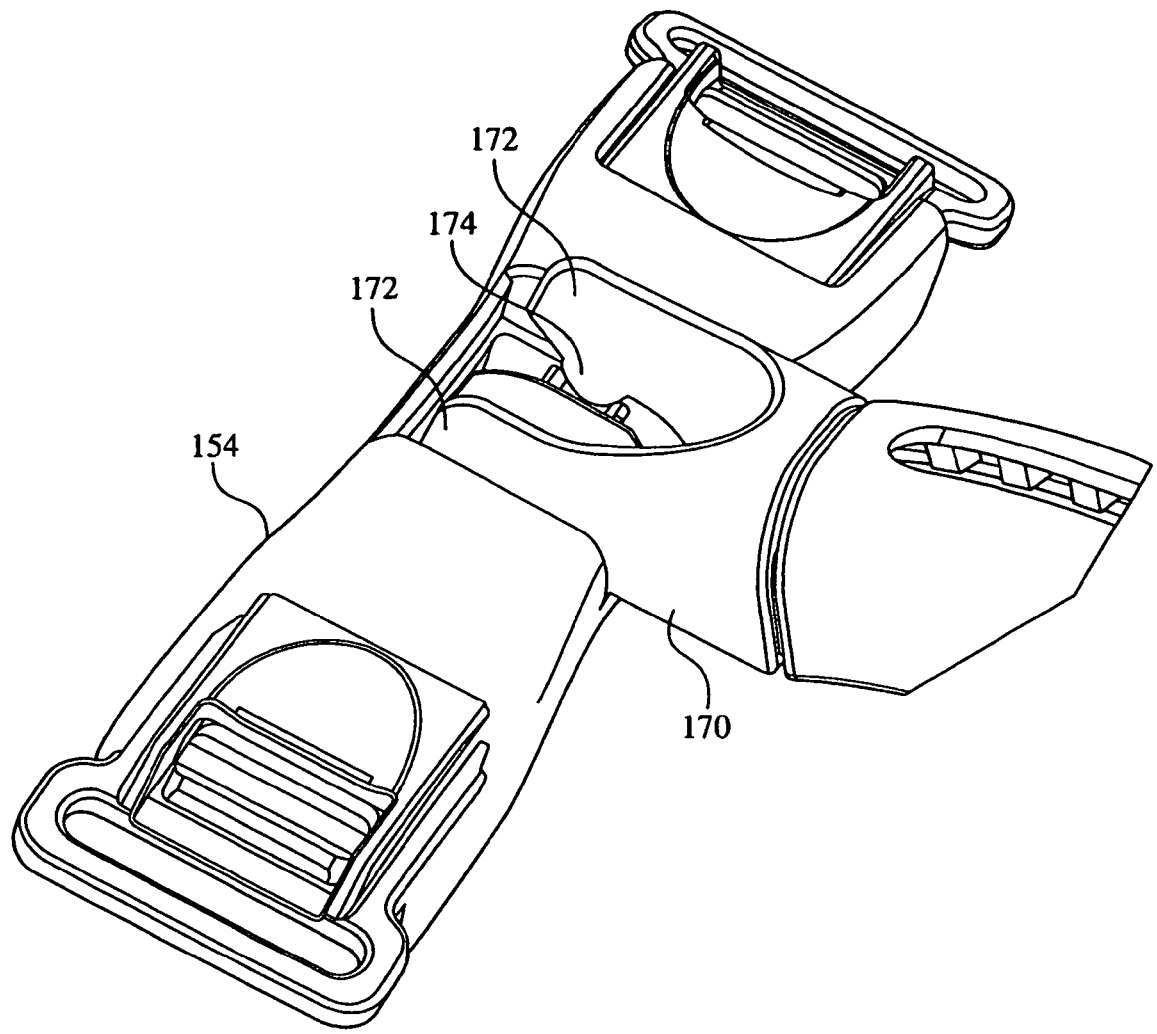
FIG. 11 is a detailed perspective view of the forehead support assembly of the patient interface device of FIG. 8.
Figure 12:
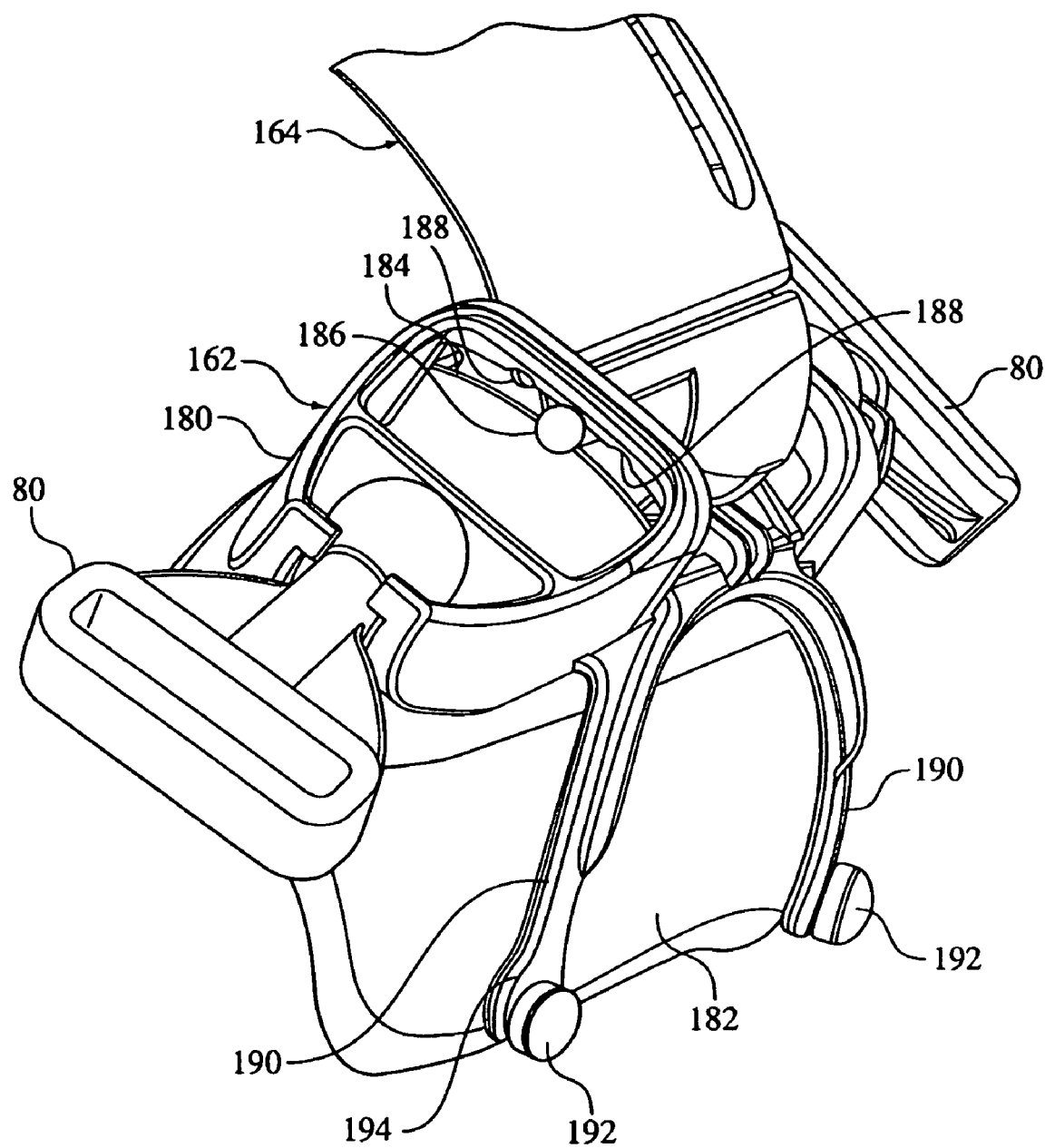
FIG. 12 is a detailed perspective view of the chin support assembly of the patient interface device of FIG. 8.
Figure 13:
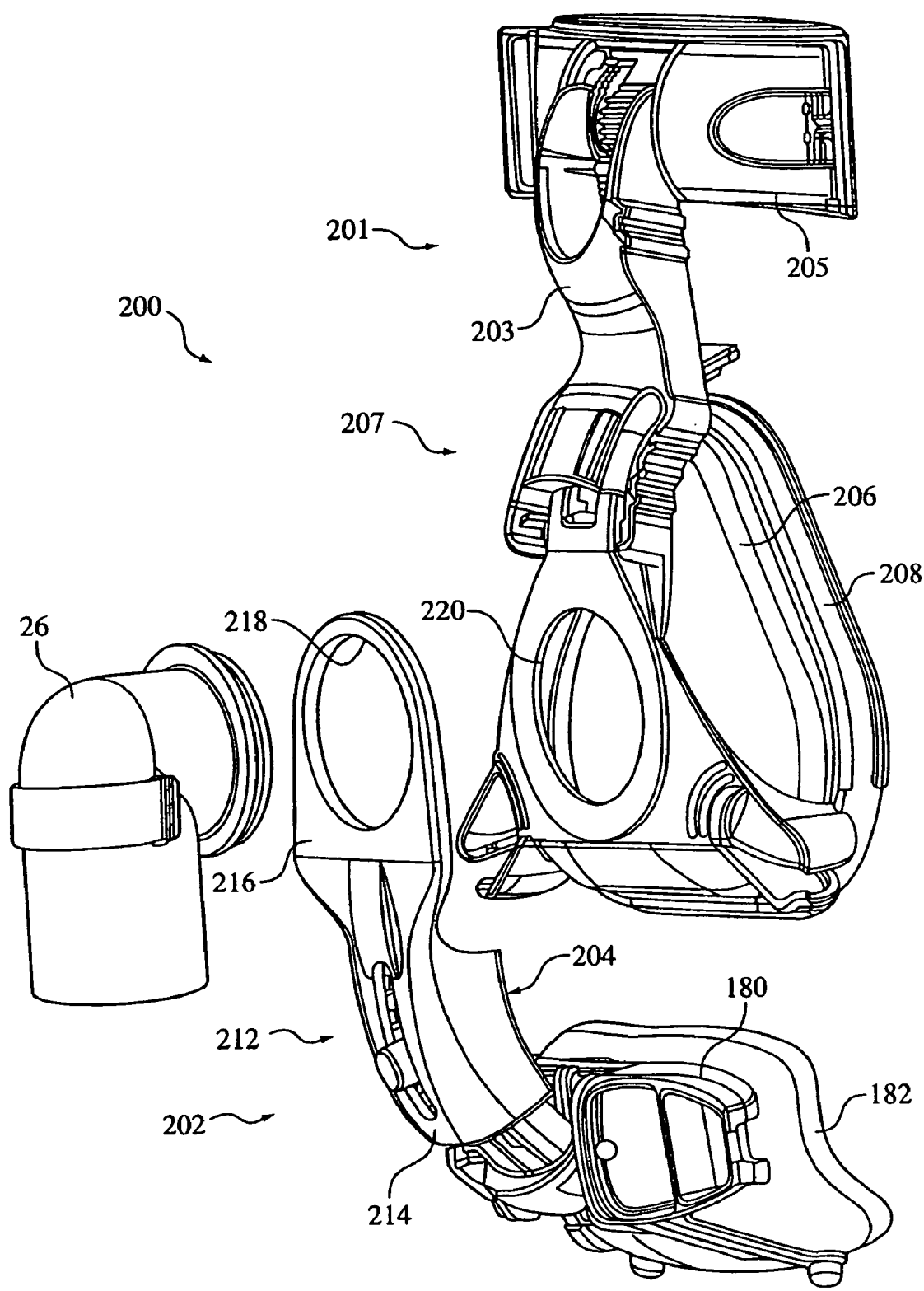
FIG. 13 is an exploded perspective view of a fifth embodiment of a patient interface device according to the present invention.
Figure 14:
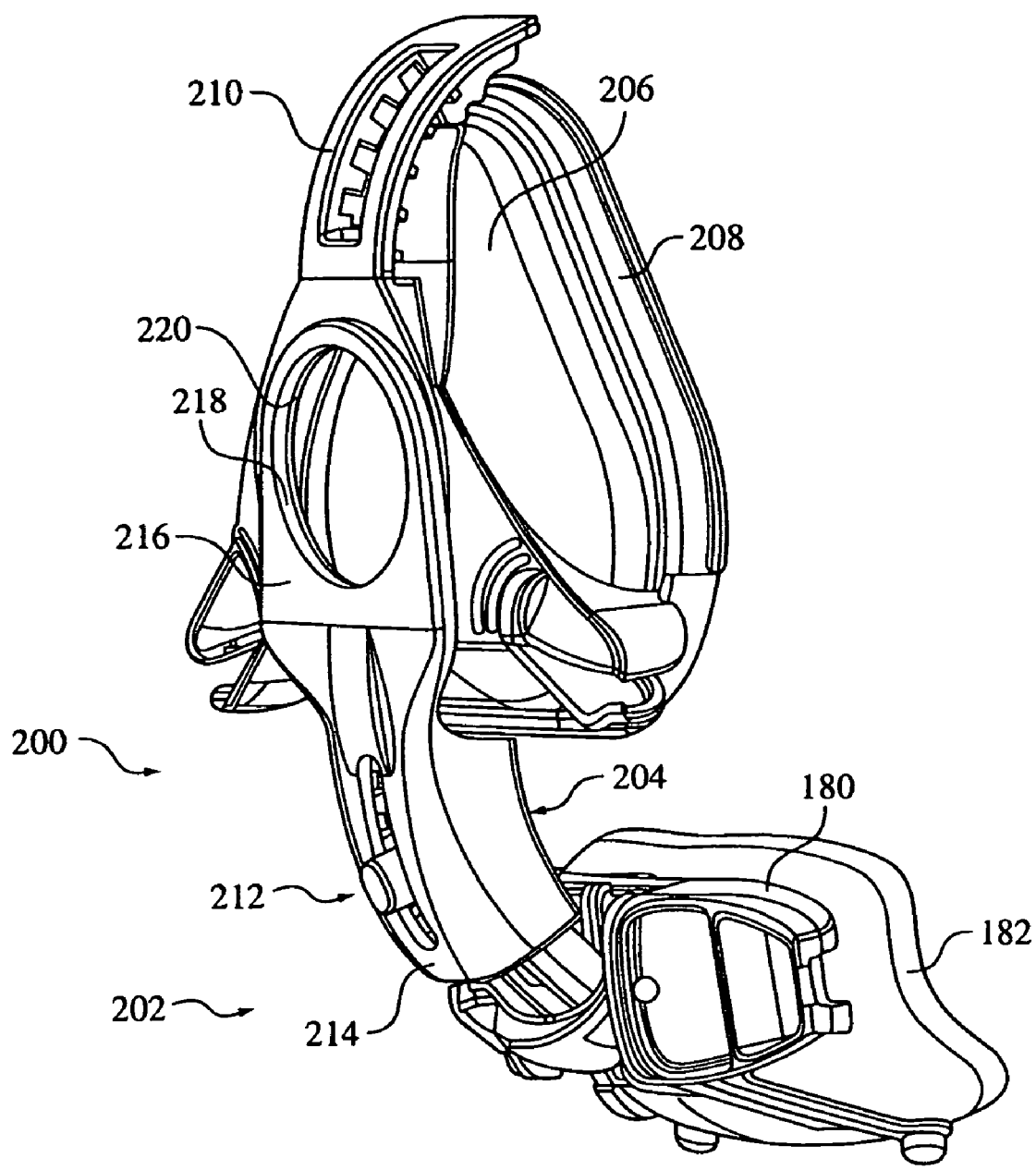
FIG. 14 is a perspective view of a portion of the patient interface device of FIG. 13.
Figure 15:
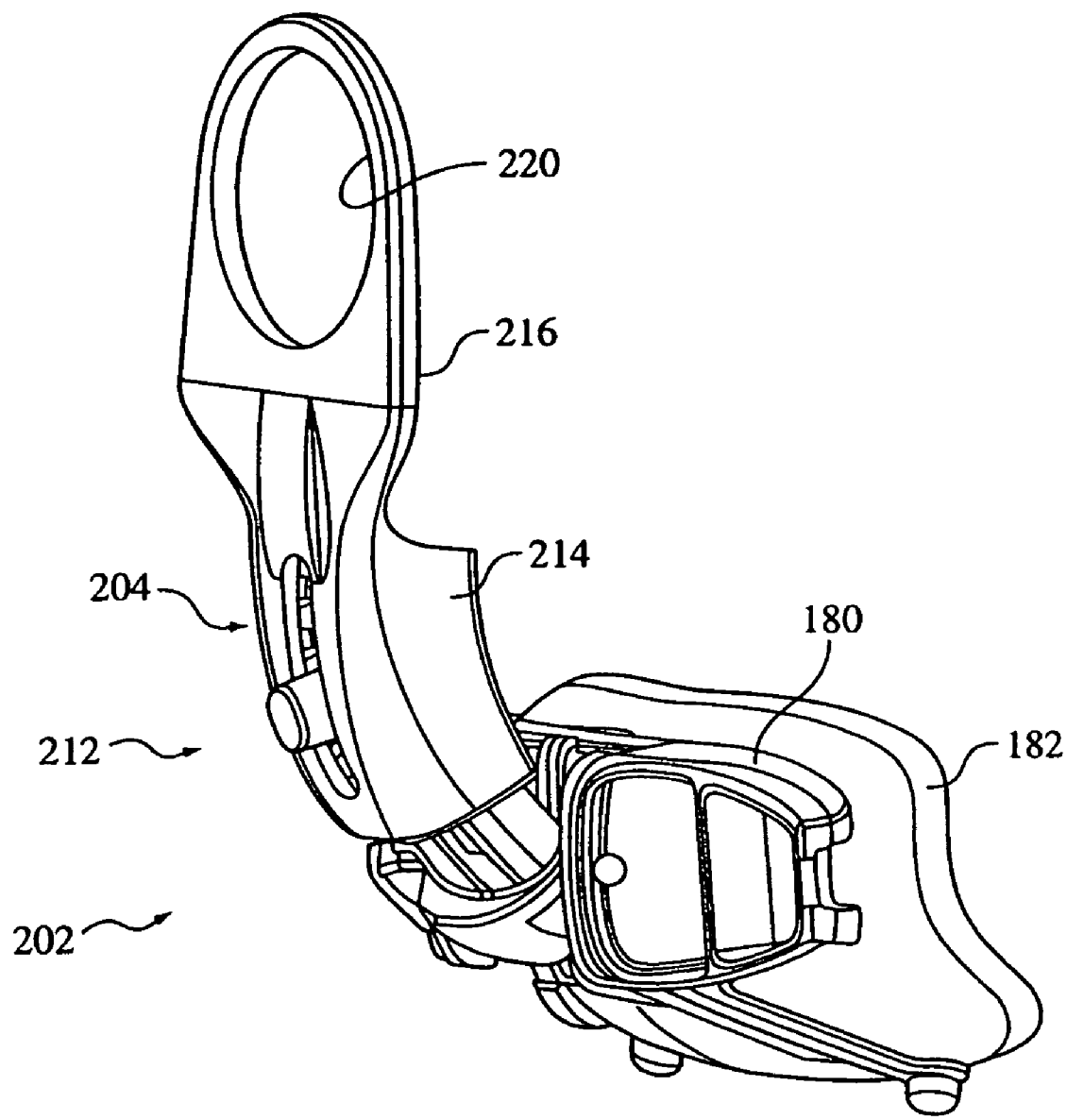
FIG. 15 is a perspective view of the chin support assembly of the patient interface device of FIG. 13.

As perhaps best shown in FIGS. 9-11, forehead support bracket 154 is pivotally attached to an upper end portion 170 of forehead support arm 156 so that the forehead support bracket rotates or rocks, as indicated by arrow H in FIG. 9, about an axis defined on or near the forehead support bracket. In this embodiment, the rocking movement of forehead support bracket 154 relative to forehead support arm 156 is not locked, so that the forehead support bracket seeks the optimum position without user intervention when the forehead support assembly is placed on the patient.

To provide the pivotal attachment in this exemplary embodiment, upper end portion 170 of forehead support arm 156 includes a pair of walls 172 that extend from the support arm. These walls are preferably slightly flexible and include a protrusion 174 that provides a pivot axis (not shown). The pivot axis is disposed in a receiving slot defined in forehead support bracket 154. Unlike the embodiment shown in FIGS. 1-4, the flexibility of the walls allows the forehead support bracket to be detached from the forehead support arm. This is particularly useful in cleaning the patient interface device, removing the mask while the headgear remains attached to the patient so that he or she does not have to readjust the headgear each time the mask shell is removed, and allowing for different sized or shaped components to be used in conjunction with one another.

Chin support bracket 162 includes a chin support frame 180 and a chin support cushion 182 that selectively attaches to the chin support frame. Chin support frame 180 in this exemplary embodiment, is attached to chin support arm 164 is a slide-and-rotate arrangement that is similar to that discussed above with respect to the attachment of the chin support bracket to the chin support arm in FIGS. 1-4. Briefly stated, chin support frame 180 includes a pair of grooves 184 that are adapted to receive a pair of protruding pivots 186 disposed on a lower end portion of chin support arm 164. A plurality of notches 188 are provided in grooves 184 to receive the protruding pivots 186 so that the pivots can be rotatably located at various locations along the length of grooves 180. Thus, the sliding function is provided by allowing the protruding pivots to move along the length of the grooves, and the rotating function is provided by allowing the protruding pivots to rest in the notches.

Chin support cushion 182 is preferably coupled to chin support frame 180 in a removable fashion. To accomplish this, the chin support cushion and frame include engaging portions that can be selectively joined to one another. One such engaging portion is provided at the center of the chin support frame, and this arrangement is perhaps best shown in FIGS. 16 and 17, and described in greater detail below. Another such engaging portion is provided by support arms 190 that extend from a bottom portion of chin support frame 180. Arms 190 also provide structural support for the relatively flexible chin support cushion. Chin support cushion 182 includes a pair of protrusions 192 that engage slots 196 (see FIG. 17) provided in a distal end portion 194 of arms 190. The flexible nature of protrusions 192 allows them to be readily inserted into and removed from the slots in end portion 194 of arms 190.

A fifth exemplary embodiment for a patient interface device 200 is illustrated in FIGS. 13-17. Like in the previous embodiments, this embodiment includes a forehead support assembly 201 having a forehead support bracket 205 and a forehead support arm 203 and a chin support assembly 202 having chin support bracket 180 and a chin support arm 204. In this illustrated embodiment, the forehead and chin support assemblies are connected to a mask shell 206 that includes a chamber for receiving a portion of user's face, such as the nose, and an opening to which the patient circuit is attached. A patient contacting cushion (not shown) is attached to an end portion 208 of mask shell 206 in a fixed or removable fashion.

One unique feature of this embodiment is the manner in which the forehead support assembly 201 is attached to mask shell 206. In the previous embodiments, the forehead support arm included an arcuate attaching member that extended from the mask shell to provide the forehead adjustment assembly. In this embodiment the arcuate attaching member is, in effect, replaced by a forehead support adjustment track 210 that is more flush with the mask shell as part of a forehead adjustment assembly 207. Forehead support arm 203 attaches to forehead support adjustment track 210 such that the forehead support arm moves along the track and is selectively lockable into positions along the track via the teeth provided in the track. This arrangement for attaching the forehead support assembly to the mask shell and details regarding forehead support arm 203 and forehead support bracket 205 and their respective attachments to one another are described in U.S. patent application Ser. No. 10/654,379 (publication no. US-2004-0045551-A1), the contents of which are incorporated herein by reference.

A second unique feature for the patient interface device of this embodiment is the manner in which chin support assembly 202 is attached to mask shell 206. As in the previous embodiments, chin support assembly 202 includes a chin adjustment assembly 212 that is defined by portions of chin support arm 204. However, instead of having an arcuate attaching member that extends from the bottom portion of the mask, chin adjustment assembly 212 and chin support arm 204 include a first attaching member 214. In addition, an arcuate support member 213 is slidably coupled to an end portion of first attaching member 214, so that chin support bracket 180 is adjustably connectable to mask shell 206.

First attaching member 214 has an end portion 216 that attaches to the mask shell by surrounding an opening 218 to which a patient circuit (not shown) is attached. More specifically, end portion 216 includes and opening 220 through which the patient circuit is inserted. When the patient circuit is inserted through opening 220 and engaged in opening 218 of mask shell 206, end portion 216 of first attachment member 214 is effectively attached to the mask shell. An advantage of this configuration is that it allows the chin support assembly to be retrofit onto existing masks. It also allows the chin support assembly to be attached to any mask in a removable fashion, whether or not retrofitted, so that a mask user can select a mask for use, and decide whether to add the chin support assembly as an optional accessory for the mask.

Figure 16:
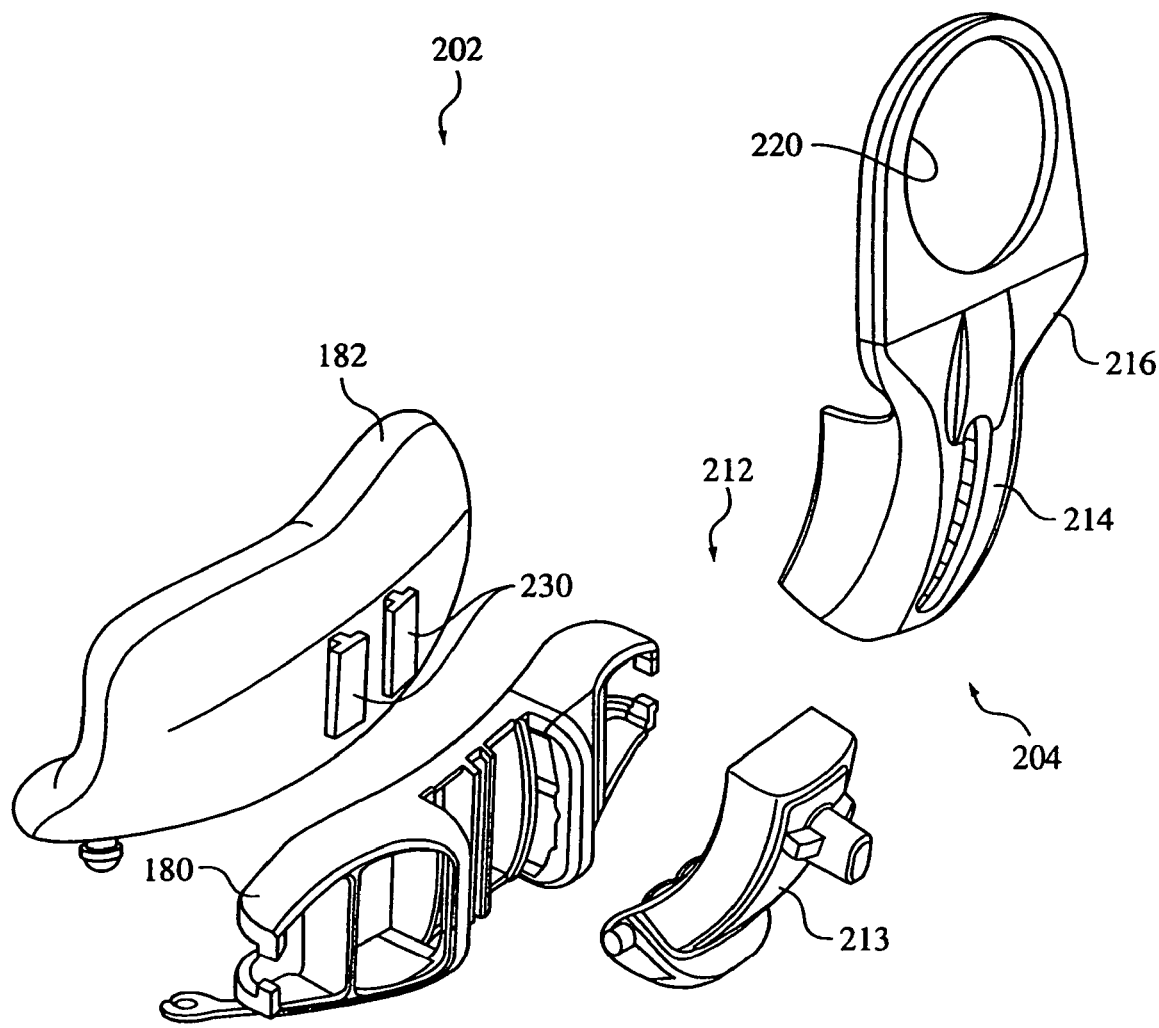
FIG. 16 is an exploded, front perspective view of the chin support assembly of the patient interface device of FIG. 13.
Figure 17:
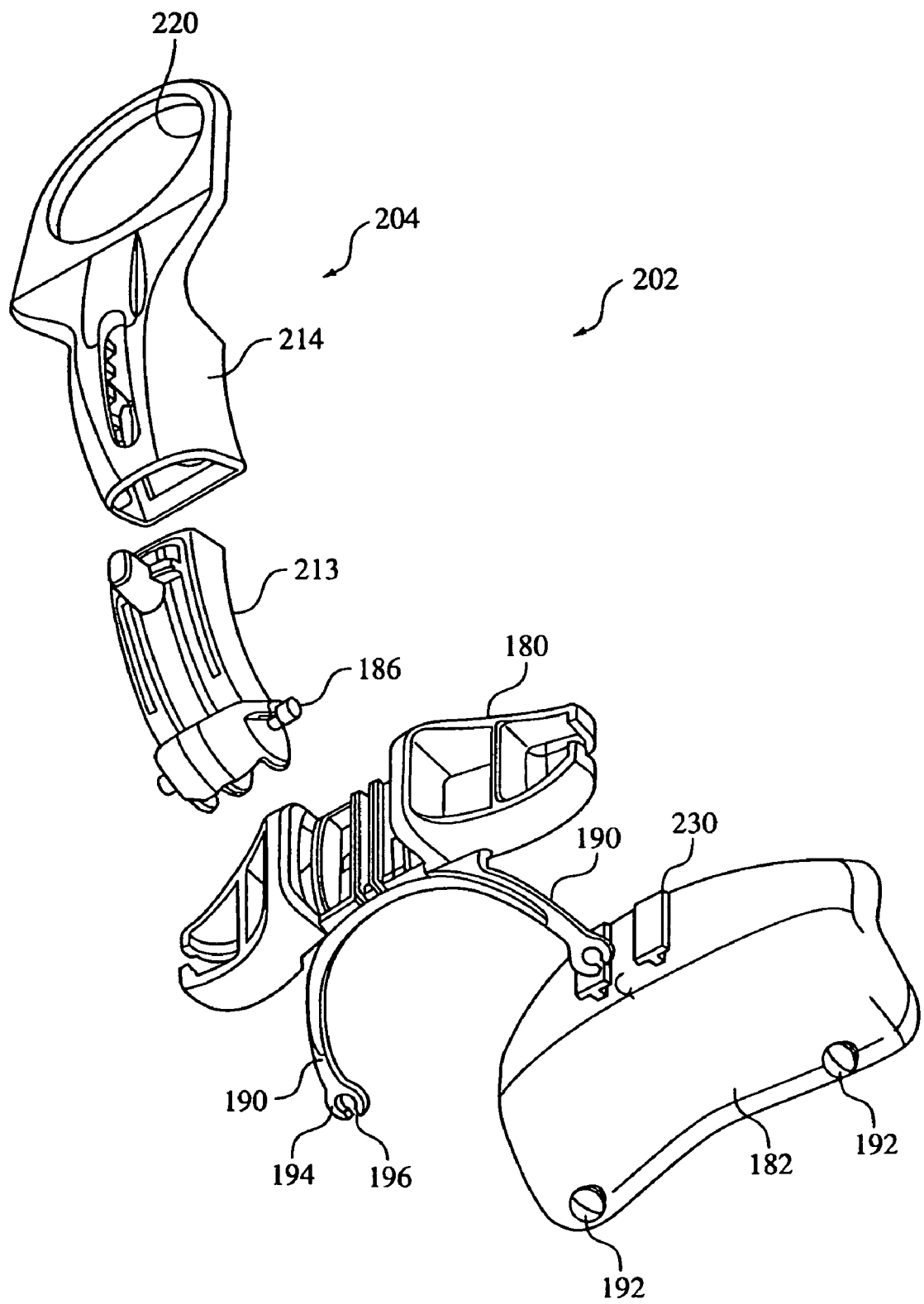
FIG. 17 is an exploded, rear perspective view of the chin support assembly of the patient interface device of FIG. 13.

As shown in FIGS. 16 and 17, chin support cushion 182 includes at least one attachment member 230 that is preferably formed from the same flexible material as the rest of the chin support cushion. Attachment members 230 are configured, sized, and arranged so that they insert into corresponding slots defined in chin support fame 180 and are retained there.

Figure 18:
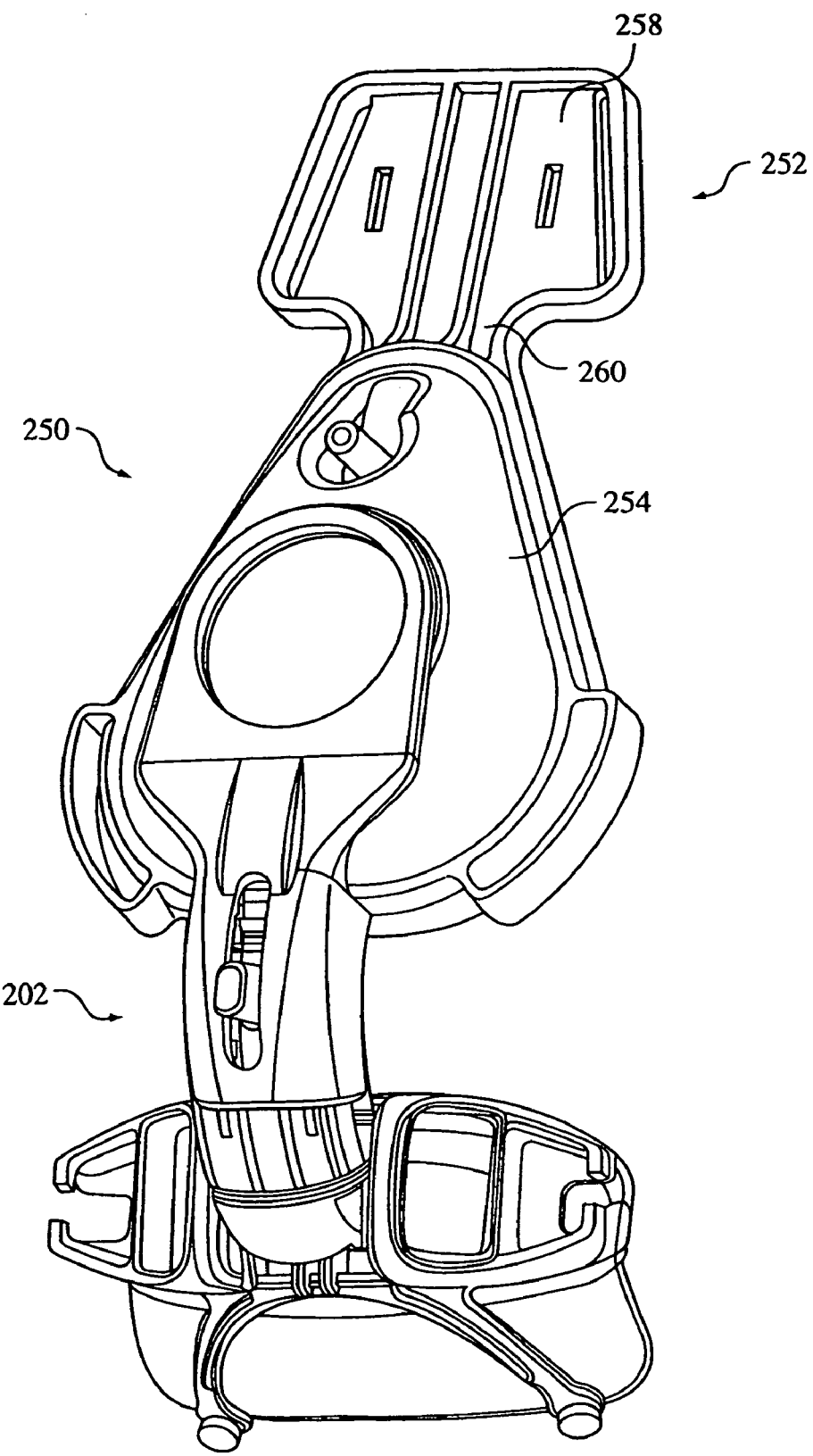
FIG. 18 is a perspective view of a sixth embodiment of a patient interface device according to the present invention.

A sixth exemplary embodiment for a patient interface device 250 is illustrated in FIG. 18. Patient interface device 250 is similar to patient interface device 200 in that it includes the same chin support assembly 202 that selectively attaches to the patient circuit that attaches to the mask shell. The primary difference between this embodiment and that shown in FIGS. 13-17 resides in the configuration for forehead support assembly 252 that is coupled to mask shell 254. More specifically, forehead support assembly 252 includes a forehead support bracket 258 and a forehead support arm 260. In this embodiment, unlike the previous embodiments, the forehead support bracket is maintained in a fixed position relative to mask shell 254. This is accomplished in this embodiment by defining forehead support bracket 258, forehead support arm 260, and mask shell 254 in one integrated piece. This embodiment clarifies that the present invention contemplates that the forehead support assembly, as well as the chin support assembly, need not provide adjustment of the forehead support bracket or the chin support bracket relative to the mask shell.

Mask shell 254 and forehead support assembly 252 shown in FIG. 18 corresponds to the patient interface device described in U.S. Pat. No. 6,467,483, the contents of which are incorporated herein by reference. It is to be understood, however, that the present invention contemplates other configurations for the forehead support assembly and mask components.

The patient interface device communicates a flow of breathing gas between the patient's airway and pressure generating device, such as a ventilator, CPAP device, or variable pressure device, e.g., an auto-titrating pressure support device or a BiPAP® device manufactured and distributed by Respironics, Inc. of Pittsburgh, Pa., in which the pressure provided to the patient varies with the patient's respiratory cycle so that a higher pressure is delivered during inspiration than during expiration or an auto-titratition pressure support system where the pressure varies with the condition of the patient, such as whether the patient is snoring or experiencing an apnea or hypopnea.

Communicating a flow of breathing gas between the patient's airway and a pressure generating device includes delivering a flow of breathing gas to the patient from the pressure generating device and exhausting a flow of gas from the patient to ambient atmosphere in the case of single-limb circuit. The system for delivering a breathing gas to a patient according to the present invention comprises a pressure or gas flow generating device 12 that produces a flow of gas, a conduit 26 having a first end portion operatively coupled to the gas flow generating device 12 and a second end portion, wherein the conduit 26 carries the flow of gas from the gas flow generating device 12 during operation of the system; a gas delivery mask assembly 10 coupled to the second end portion of the conduit; and a headgear. It is to be understood that other accessories used in a pressure support system, such as a humidifier, pressure sensor, flow sensor, temperature sensor, humidity sensor, bacteria filter, etc. can be used in conjunction with the patient interface device of the present invention.

In the illustrated embodiment, the adjustment assemblies FIGS. 1-6 and 8-18 are configured to allow for curvilinear movement of the forehead and chin supports relative to the mask shell. It is to be understood, however, that the present invention contemplates that the adjustment assemblies can provided other patterns of translational movement of the forehead and chin supports relative to the mask shell. For example, the attaching member can have an "S" shaped pattern, or a "J" shaped pattern so that the support is moveable in an "S" or "J" pattern relative to the mask shell.

In the above-described embodiments for the patient interface device of the present invention, the pads that attach to the forehead support assemblies and the chin support assemblies and that contact the surface of the patient were discussed briefly. It is to be understood that the present invention contemplates attaching any conventional pad to the present forehead support assemblies and the chin support assemblies. For example, various types of patient contacting pads suitable for use with the present invention is described in U.S. patent application Ser. No. 10/884,060 (publication no. US-2005-0011522-A1), the contents of which are incorporated herein by reference. Those skilled in the art will understand, however, that other pads, and materials for the pad (such as gels, foams, silicon, and fabric) can be used in conjunction with the patient interface device of the present invention.

It can also be appreciated that the description of the present invention, while discussing some different embodiments for the seal and mask, is not intended to be an exhaustive listing of the seals and masks suitable for use with the patient interface device of the present invention. On the contrary, those skilled in the art can appreciate that the mask shell can have almost any configuration or size and still be used in conjunction with the patient interface device of the present invention. Moreover, the mask shell and cushion can be combined into a single structure to which the forehead and chin support assemblies are mounted and still remain within the teachings of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface comprising:
a mask shell having a longitudinal axis;
a sealing member coupled to the mask shell;
a forehead support assembly associated with the mask shell, wherein the forehead support assembly includes a forehead pad, and wherein the forehead support assembly is adjustable relative to the mask shell generally along the longitudinal axis so that a position of the forehead pad relative to the mask shell can be adjusted; and
a chin support assembly associated with the mask shell, wherein the chin support assembly includes a chin pad, and wherein the chin support assembly is adjustable relative to the mask shell generally along the longitudinal axis so that a position of the chin pad relative to the mask shell can be adjusted to control a distance between the chin pad and the mask shell.

2. The patient interface of claim 1, wherein the forehead support assembly comprises:
an attaching member coupled to the mask shell; and
a support member moveably coupled to the attaching member.

3. The patient interface of claim 2, wherein the attaching member and the support member have complimentary shapes such that at least a portion of one of the attaching member and the support member is slidable within at least a portion of a remaining other of the attaching member and the support member generally along the longitudinal axis.

4. The patient interface of claim 3, wherein the attaching member comprises a track member operatively coupled to the mask shell and the support member includes a portion adapted to engage the track member.

5. The patient interface of claim 1, wherein the forehead support assembly comprises:
a forehead support arm operatively coupled to the mask shell; and
a forehead support bracket operatively coupled to the forehead support arm, wherein the forehead pad is operatively coupled to the forehead support bracket.

6. The patient interface of claim 5, wherein the forehead support bracket is movably coupled to the forehead support arm.

7. The patient interface of claim 5, wherein the forehead support arm is a flexible member.

8. The patient interface of claim 7, wherein a position of the forehead support bracket along a length of the flexible member is adjustable.

9. The patient interface of claim 5, wherein the forehead support bracket is maintained in a fixed position relative to the mask shell via the forehead support arm.

10. The patient interface of claim 1, wherein the forehead support assembly, the chin support assembly, or both the forehead support assembly and the chin support assembly are selectively attachable to the mask shell.

11. The patient interface of claim 1, wherein the chin support assembly comprises:
an attaching member operatively coupled the mask shell; and
a support member moveably coupled to the attaching member.

12. The patient interface of claim 11, wherein the attaching member and the support member have complimentary shapes such that at least a portion of one of the attaching member and the support member is slidable within at least a portion of a remaining other of the attaching member and the support member generally along the longitudinal axis.

13. The patient interface of claim 11, wherein the attaching member comprises a track member operatively coupled to the mask shell and the support member includes a portion adapted to engage the track member.

14. The patient interface of claim 1, wherein the chin support assembly comprises:
   a chin support arm operatively coupled to the mask shell; and
   a chin support bracket operatively coupled the chin support arm, wherein the chin pad is operatively coupled to the chin support bracket.

15. The patient interface of claim 14, wherein the chin support bracket is movably mounted on the chin support arm.

16. The patient interface of claim 14, wherein the chin support arm is a flexible member.

17. The patient interface of claim 16, wherein a position of the chin support bracket along a length of the flexible member is adjustable.

18. The patient interface of claim 14, wherein the chin support bracket is maintained in a fixed position relative to and the mask shell via the chin support arm.

19. The patient interface of claim 1, wherein the forehead support assembly comprises:
   a forehead support arm operatively coupled to the mask shell; and
   a forehead support bracket mounted on the forehead support arm, and wherein the chin support assembly comprises:
   a chin support arm operatively coupled to the mask shell; and
   a chin support bracket mounted on the chin support arm.

20. The patient interface of claim 19, wherein the forehead support bracket is movably mounted on the forehead support arm, and wherein the chin support bracket is movably mounted on the chin support arm.

* * * * *